US011172937B2

(12) United States Patent
Saatchi et al.

(10) Patent No.: US 11,172,937 B2
(45) Date of Patent: Nov. 16, 2021

(54) TISSUE COMPRESSION DEVICE WITH PRESSURE INDICATOR

(71) Applicant: Medtronic Vascular, Inc., Santa Rosa, CA (US)

(72) Inventors: Sanaz Saatchi, San Francisco, CA (US); Joseph Berglund, Santa Rosa, CA (US); Conor Flannery, San Rafael, CA (US); Mark Hoff, Windsor, CA (US); Brian Joseph Mason, Palo Alto, CA (US); Yusuke Miyashita, San Mateo, CA (US); Remy O'Leary Pieron, San Francisco, CA (US); Justin Williams, San Francisco, CA (US)

(*) Notice: Subject to any disclaimer, the term of this patent is extended or adjusted under 35 U.S.C. 154(b) by 442 days.

(21) Appl. No.: 16/047,447

(22) Filed: Jul. 27, 2018

(65) Prior Publication Data

US 2018/0344324 A1    Dec. 6, 2018

Related U.S. Application Data

(62) Division of application No. 15/238,461, filed on Aug. 16, 2016, now Pat. No. 10,034,671, which is a
(Continued)

(51) Int. Cl.
*A61B 17/132*     (2006.01)
*A61H 9/00*       (2006.01)
(Continued)

(52) U.S. Cl.
CPC .......... *A61B 17/1325* (2013.01); *A61B 17/12* (2013.01); *A61B 17/132* (2013.01);
(Continued)

(58) Field of Classification Search
CPC .............. A61B 17/132; A61B 17/1322; A61B 17/1325; A61B 17/1327; A61B 17/135;
(Continued)

(56) References Cited

U.S. PATENT DOCUMENTS

| 721,162 A | 2/1903 | Denain |
|---|---|---|
| 1,870,052 A | 11/1930 | Jones |

(Continued)

FOREIGN PATENT DOCUMENTS

| CN | 201094648 Y | 8/2008 |
|---|---|---|
| CN | 201205292 Y | 3/2009 |

(Continued)

OTHER PUBLICATIONS

Air-Band Radial Compression Device, Instructions for use, pp. 1-88, 2013.
(Continued)

*Primary Examiner* — Wade Miles
*Assistant Examiner* — Kankindi Rwego

(57) ABSTRACT

Tissue compression devices having pressure indicators and methods of using the same. The tissue compression devices provide feedback to a user with respect to the pressure being applied to selected tissue at a selected location such as a radial artery to assist the user in applying the desired amount of pressure to the tissue (such as the pressure needed to achieve hemostasis at an access site). The pressure indication may be provided by a ring indicator that moves between two configurations (e.g., a concave configuration and a convex configuration), a bellow chamber in a housing, a bladder located below a bladder window, etc.

18 Claims, 20 Drawing Sheets

Related U.S. Application Data division of application No. 14/261,758, filed on Apr. 25, 2014, now Pat. No. 9,439,827.

(60) Provisional application No. 61/895,940, filed on Oct. 25, 2013, provisional application No. 61/895,953, filed on Oct. 25, 2013, provisional application No. 61/895,944, filed on Oct. 25, 2013.

(51) Int. Cl.
*A61B 17/135* (2006.01)
*A61F 5/32* (2006.01)
*A61H 1/00* (2006.01)
*A61B 17/12* (2006.01)
*A61B 17/00* (2006.01)

(52) U.S. Cl.
CPC ......... *A61B 17/135* (2013.01); *A61H 1/006* (2013.01); *A61H 9/0092* (2013.01); *A61B 2017/00243* (2013.01); *A61B 2017/00778* (2013.01); *A61B 2017/12004* (2013.01); *A61F 5/32* (2013.01)

(58) Field of Classification Search
CPC . A61B 17/1355; A61B 5/021; A61B 5/02141; A61B 5/022; A61B 17/12; A61B 2017/00243; A61B 2017/00778; A61B 2017/12004; A61H 9/0078; A61H 9/0085; A61H 9/0092; A61H 1/006; A61F 5/30; A61F 5/32; A61F 5/34
USPC ........................................................ 606/200
See application file for complete search history.

(56) References Cited

U.S. PATENT DOCUMENTS

| | | | |
|---|---|---|---|
| 1,824,516 A | 9/1931 | Tyvand | |
| 2,271,927 A | 6/1938 | Saighman | |
| 2,316,158 A | 4/1943 | Eschner | |
| 2,332,107 A | 10/1943 | Nieburgs | |
| 2,344,021 A | 3/1944 | Bouziane | |
| 2,387,642 A | 10/1945 | Calhoun | |
| 3,171,410 A | 3/1965 | Towle, Jr. et al. | |
| 3,620,209 A | 11/1971 | Kravitz | |
| 3,654,931 A | 4/1972 | Hazlewood | |
| 4,005,709 A | 2/1977 | Laerdal | |
| 4,224,945 A | 9/1980 | Cohen | |
| 4,233,980 A | 11/1980 | McRae et al. | |
| 4,297,996 A | 11/1981 | Uriza | |
| 4,480,638 A | 11/1984 | Schmid | |
| 4,834,802 A | 5/1989 | Prier | |
| 5,010,902 A | 4/1991 | Rambo | |
| 5,181,522 A | 1/1993 | McEwen | |
| 5,263,966 A * | 11/1993 | Daneshvar ............... A61F 5/34 606/201 |
| 5,269,803 A | 12/1993 | Geary et al. | |
| 5,307,811 A | 5/1994 | Sigwad et al. | |
| 5,433,724 A | 7/1995 | Kawasaki | |
| 5,464,420 A | 10/1995 | Hori | |
| 5,486,194 A | 1/1996 | Kawasaki | |
| 5,507,721 A | 4/1996 | Shipped | |
| 5,601,597 A | 2/1997 | Arrowood et al. | |
| 5,660,182 A | 8/1997 | Kuroshaki et al. | |
| 5,690,610 A | 11/1997 | Ito et al. | |
| 5,695,520 A | 12/1997 | Bruckner et al. | |
| 5,709,647 A | 1/1998 | Ferber | |
| 5,728,120 A | 3/1998 | Shani et al. | |
| 5,753,821 A | 5/1998 | Chou | |
| 5,792,173 A | 8/1998 | Breen et al. | |
| 5,871,499 A | 2/1999 | Hahn et al. | |
| 5,873,890 A | 2/1999 | Porat | |
| 5,968,072 A | 10/1999 | Hite et al. | |
| 6,068,646 A | 5/2000 | Lam | |
| 6,077,241 A | 6/2000 | Fareed | |
| 6,217,601 B1 | 4/2001 | Chao | |
| 6,336,901 B1 | 1/2002 | Itonaga et al. | |
| 6,361,496 B1 | 3/2002 | Zikorus et al. | |
| 6,422,086 B1 | 7/2002 | Dromms et al. | |
| 6,503,266 B1 | 1/2003 | Sjogren et al. | |
| 6,506,206 B1 | 1/2003 | Guzman et al. | |
| 6,593,508 B1 | 7/2003 | Harder | |
| 6,663,653 B2 | 12/2003 | Akerfeldt | |
| 6,694,821 B2 | 2/2004 | Yamakoshi et al. | |
| 6,746,406 B2 | 6/2004 | Lia | |
| 6,746,470 B2 | 6/2004 | McEwen et al. | |
| 6,752,820 B1 | 6/2004 | Hafemann | |
| 6,758,821 B2 | 7/2004 | Itonaga et al. | |
| 6,827,727 B2 | 12/2004 | Stalemark et al. | |
| 6,833,001 B1 | 12/2004 | Chao | |
| 7,000,483 B2 | 2/2006 | Pekar et al. | |
| 7,135,032 B2 | 11/2006 | Akerfeldt | |
| 7,247,163 B2 | 7/2007 | Akerfeldt | |
| 7,281,430 B2 | 10/2007 | Pekar et al. | |
| 7,329,270 B2 | 2/2008 | Akerfeldt et al. | |
| 7,445,625 B2 | 11/2008 | Akerfeldt | |
| 7,498,477 B2 | 3/2009 | Wada et al. | |
| 7,582,102 B2 | 9/2009 | Heinz et al. | |
| 7,611,469 B2 | 11/2009 | Karo | |
| 7,618,384 B2 | 11/2009 | Nardi | |
| 7,637,921 B2 | 12/2009 | Akerfeldt et al. | |
| 7,652,190 B2 | 1/2010 | Johnson | |
| 7,763,046 B2 | 7/2010 | Schouten et al. | |
| 7,780,612 B2 | 8/2010 | Ross et al. | |
| 7,927,295 B2 | 4/2011 | Bates et al. | |
| 7,955,362 B2 | 6/2011 | McEwen | |
| 8,034,009 B2 | 10/2011 | Bates et al. | |
| 8,114,026 B2 | 2/2012 | Leschinsky | |
| 8,137,378 B2 | 3/2012 | McEwen | |
| 8,277,483 B2 | 10/2012 | Teeslink et al. | |
| 8,328,741 B2 | 12/2012 | Ganapathy | |
| 8,353,927 B2 | 1/2013 | Lampropoulos et al. | |
| 8,357,831 B2 | 1/2013 | Buckman et al. | |
| 8,439,943 B2 | 5/2013 | Chao | |
| 8,481,805 B2 | 7/2013 | Wada et al. | |
| 8,524,974 B2 | 9/2013 | Wada et al. | |
| 8,657,850 B2 | 2/2014 | McNeese | |
| 8,759,603 B2 | 6/2014 | Wada et al. | |
| 8,834,517 B2 | 9/2014 | Croushorn et al. | |
| 8,845,680 B2 | 9/2014 | Lampropoulos et al. | |
| 8,870,781 B2 | 10/2014 | Lee et al. | |
| 8,900,266 B2 | 12/2014 | Heston | |
| 8,905,957 B1 | 12/2014 | Kozersky | |
| 9,021,883 B2 | 5/2015 | Wang | |
| D733,305 S | 6/2015 | Miyashita et al. | |
| 2003/0055453 A1 | 3/2003 | Akerfeldt | |
| 2003/0114881 A1 | 6/2003 | Stalemark et al. | |
| 2003/0139673 A1 | 7/2003 | Vivenzio et al. | |
| 2003/0139696 A1 | 7/2003 | Boukanov et al. | |
| 2003/0199922 A1 | 10/2003 | Buckman | |
| 2004/0039413 A1 | 2/2004 | Akerfeldt et al. | |
| 2004/0068290 A1 | 4/2004 | Bates et al. | |
| 2004/0092999 A1 | 5/2004 | Lojewski | |
| 2004/0143289 A1 | 7/2004 | Zahler et al. | |
| 2005/0131326 A1 | 6/2005 | Bates et al. | |
| 2007/0191881 A1 | 8/2007 | Amisar et al. | |
| 2007/0293888 A1 | 12/2007 | Harren et al. | |
| 2008/0125684 A1 | 5/2008 | Nardi et al. | |
| 2008/0216213 A1 | 9/2008 | Lin et al. | |
| 2008/0312682 A1 | 12/2008 | Shams et al. | |
| 2009/0234261 A1 | 9/2009 | Singh | |
| 2009/0318952 A1 | 12/2009 | Bates et al. | |
| 2009/0318953 A1 | 12/2009 | Bates et al. | |
| 2010/0241032 A1 | 9/2010 | Lee et al. | |
| 2011/0028934 A1 | 2/2011 | Buckman | |
| 2011/0130739 A1 | 6/2011 | Fitzpatrick et al. | |
| 2011/0202089 A1 | 8/2011 | Sun | |
| 2012/0046582 A1 | 2/2012 | Hopman et al. | |
| 2012/0053617 A1 | 3/2012 | Benz et al. | |
| 2012/0116444 A1 | 5/2012 | Zodnik et al. | |
| 2012/0150215 A1 | 6/2012 | Donald | |
| 2012/0191127 A1 | 7/2012 | Guillot | |
| 2012/0191128 A1 | 7/2012 | Teeslink et al. | |

(56) References Cited

U.S. PATENT DOCUMENTS

| | | |
|---|---|---|
| 2012/0215252 A1 | 8/2012 | Adenmark |
| 2012/0221041 A1 | 8/2012 | Hansson et al. |
| 2012/0226306 A1 | 9/2012 | Jackson et al. |
| 2012/0232579 A1 | 9/2012 | Lee |
| 2012/0238934 A1 | 9/2012 | During |
| 2012/0271179 A1 | 10/2012 | Adenmark |
| 2012/0296369 A1 | 11/2012 | Atthoff et al. |
| 2012/0298116 A1 | 11/2012 | Haines et al. |
| 2013/0123836 A1 | 5/2013 | Lampropoulos et al. |
| 2013/0237866 A1 | 9/2013 | Cohen et al. |
| 2013/0245674 A1 | 9/2013 | Satoshi et al. |
| 2014/0012313 A1 | 1/2014 | Finkielsztein et al. |
| 2014/0018845 A1 | 1/2014 | Lampropoulos et al. |
| 2014/0031861 A1 | 1/2014 | Teeslink et al. |
| 2014/0094731 A1 | 4/2014 | Serola |
| 2014/0142615 A1 | 5/2014 | Corrigan |
| 2015/0073326 A1 | 3/2015 | Shih |
| 2015/0119773 A1 | 4/2015 | Flannery et al. |
| 2015/0119925 A1 | 4/2015 | Saatchi et al. |
| 2015/0119926 A1 | 4/2015 | Saatchi et al. |
| 2015/0201948 A1 | 7/2015 | Kornowski et al. |

FOREIGN PATENT DOCUMENTS

| | | |
|---|---|---|
| CN | 201551362 U | 8/2010 |
| CN | 10192666 | 12/2010 |
| CN | 201691993 | 1/2011 |
| CN | 201806747 U | 4/2011 |
| CN | 201861701 | 6/2011 |
| CN | 102475560 A | 5/2012 |
| CN | 202821487 U | 3/2013 |
| CN | 202892036 U | 4/2013 |
| CN | 202960638 U | 6/2013 |
| CN | 203059815 | 7/2013 |
| EP | 0264848 | 4/1988 |
| EP | 0462088 | 12/1991 |
| EP | 0837653 | 4/1998 |
| EP | 1256313 | 11/2002 |
| EP | 1382306 | 1/2004 |
| EP | 2070483 | 6/2009 |
| EP | 1455659 | 3/2010 |
| EP | 2245998 | 11/2010 |
| EP | 2647359 | 3/2014 |
| EP | 2677945 | 11/2014 |
| GB | 190912486 | 3/1910 |
| GB | 239717 | 9/1925 |
| JP | S5248293 | 4/1977 |
| JP | 2005318998 | 11/2005 |
| JP | 2012010823 | 1/2012 |
| JP | 2012010825 | 1/2012 |
| JP | 2012034821 | 2/2012 |
| JP | 2012040114 | 3/2012 |
| JP | 2013078529 | 2/2013 |
| JP | 5326160 | 10/2013 |
| JP | 2015088028 | 4/2015 |
| WO | WO97/18763 | 5/1997 |
| WO | WO98/46144 | 10/1998 |
| WO | WO03/082127 | 10/2003 |
| WO | 2005091718 A2 | 5/2006 |
| WO | WO2011090429 | 7/2011 |
| WO | WO2012/129146 | 9/2012 |
| WO | WO2014018280 | 1/2014 |
| WO | WO2014027347 | 2/2014 |
| WO | WO2014075627 | 5/2014 |
| WO | WO2015001198 | 1/2015 |
| WO | WO2015060966 | 4/2015 |
| WO | WO2015060967 | 4/2015 |
| WO | WO2015061016 | 4/2015 |

OTHER PUBLICATIONS

PCT International Search Report and The Written Opinion, PCT/US2014/056831, dated Feb. 12, 2015.

PCT International Search Report and The Written Opinion, PCT/US2014/056836, dated Jan. 5, 2015.

Chinese Office Action dated Dec. 23, 2020 corresponding to Chinese Patent Application No. 201910035574.5.

* cited by examiner

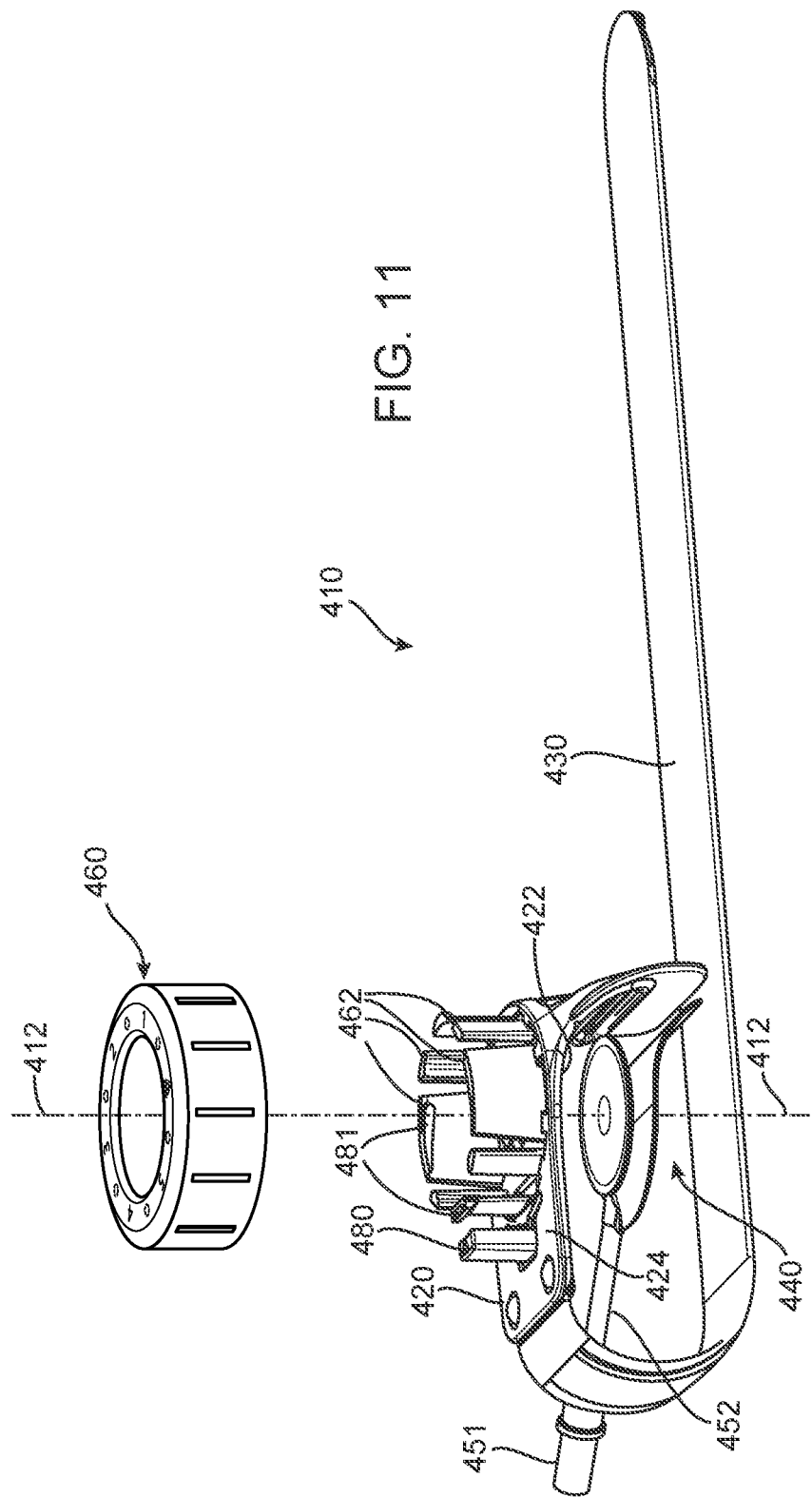

TISSUE COMPRESSION DEVICE WITH PRESSURE INDICATOR

CROSS-REFERENCE TO RELATED APPLICATIONS

The present application is a Division of U.S. patent application Ser. No. 15/238,461, filed Aug. 16, 2016, now allowed, which is a Division of U.S. patent application Ser. No. 14/261,758, filed Apr. 25, 2014, now U.S. Pat. No. 9,439,827, which claims the benefit under 35 U.S.C § 119 of U.S. Provisional Patent Application No. 61/895,940; U.S. Provisional Patent Application No. 61/895,953; and U.S. Provisional Patent Application No. 61/895,944, all of which were filed on Oct. 25, 2013 and are incorporated by reference herein.

Tissue compression devices having pressure indicators and methods of using the same are described herein.

BACKGROUND

The diagnosis and treatment of coronary artery disease is now often accomplished using vascular delivery apparatus and techniques. Vascular delivery may provide a variety of advantages because access to desired locations within a patient's body may be obtained without the need for general anesthetic or more invasive surgical techniques. Access to peripheral arteries may be accomplished using a sheath having a hemostatic valve that is inserted into the peripheral artery. A catheter or other device can then be introduced into the vasculature of the patient through that sheath to the desired location within the vasculature.

Access for these percutaneous coronary procedures may be obtained through a radial artery of the patient. Access through a radial artery may provide a number of advantages including improved patient mobilization and reduced cost. The use of a distal radial artery may, for example, allow for compression to be directly applied to the artery to achieve and maintain hemostasis.

One potential complication with any arterial access is, however, achieving hemostasis during and/or after a procedure. Arterial blood flow is pulsatile in nature and may present challenges to any practitioner seeking to achieve hemostasis at an arterial access site. Upon completion of a procedure and after removal of a catheter or other device located in the access site, pressure may be applied to the access site to achieve hemostasis and close the access site. Applying pressure at or at a point slightly upstream of the access site is one technique that may be used for achieving hemostasis. In many instances, continuous pressure may be needed to achieve hemostasis at the access site. Although it may be advantageous for the pressure to remain constant, in some instances a reduction in the level of applied pressure may be advantageous after an initially higher level of pressure is applied to the access site. Gradual reduction in the compression pressure may allow blood to flow through the artery of the access site to allow blood to reach tissue downstream from the access site. That blood flowing through the artery can, in some instances, improve clotting to achieve hemostasis without continuing application of compression.

SUMMARY

Tissue compression devices having pressure indicators and methods of using the same are described herein.

The tissue compression devices described herein provide feedback to a user with respect to the pressure being applied to selected tissue at a selected location on a patient (e.g., pressure applied over a radial artery to assist the user in applying the desired amount of pressure needed to achieve hemostasis at an access site). Although the tissue compression devices and methods described herein may be used to apply pressure to selected tissue at any selected location on a patient, the tissue compression devices may be particularly well-suited to apply pressure to tissue that includes a radial artery or other blood vessel that may, in one or more embodiments, be used as an access site for a percutaneous procedure.

In one or more embodiments, the tissue compression devices described herein may include a ring indicator that moves between two configurations, e.g., a concave configuration and a convex configuration, when a selected amount of pressure is being applied to an access site. In one or more embodiments, the ring indicator may include an indicator surface that is visible in only one of the configurations. Furthermore, in one or more embodiments, the ring indicator may provide an audible indication as it moves between the concave and convex configurations described herein.

In addition to the ring indicators described in connection with one or more illustrative embodiments of tissue compression devices described herein, other pressure indicators may be used and are described herein including, e.g., a pressure indicators that includes a bellows in a housing, etc.

In one or more embodiments, the tissue compression devices described herein may include a rotating mechanism (e.g., a dial) by which the amount of pressure applied to an access site by the bladder can be incrementally varied to provide a user with the ability to increase or decrease pressure as needed.

In a first aspect, one or more embodiments of a tissue compression device as described herein may include: a base comprising a bottom surface and a top surface, wherein the base comprises a bladder orifice formed through the base from the bottom surface to the top surface; retention structure attached to the base, the retention structure configured to retain the base over a selected location, wherein the bottom surface of the base is configured to face selected tissue at the selected location and wherein the top surface of the base is configured to face away from the selected tissue when the base is retained over the selected location; a bladder operably attached to the base, wherein a lower surface of the bladder faces the selected tissue when the retention structure retains the base over the selected location, and wherein an upper surface of the bladder faces away from the lower surface of the bladder; a ring indicator positioned above and in contact with the upper surface of the bladder, wherein the ring indicator is in a concave configuration, wherein a force exerted by the upper surface of the bladder on the ring indicator moves the ring indicator from the concave configuration to a convex configuration, and wherein an inner edge of the indicator ring is further away from the bottom surface of the base when the ring indicator is in the convex configuration than when the ring indicator is in the concave configuration; wherein the tissue compression device defines a compression axis extending through the upper surface of the bladder, the bladder orifice in the base, and the lower surface of the bladder when the base is retained over the selected location by the retention structure.

In one or more embodiments of the tissue compression devices described herein, the ring indicator is configured to move from the concave configuration to the convex configuration when fluid pressure in the bladder reaches a selected level.

In one or more embodiments of the tissue compression devices described herein, the ring indicator comprises an indicator surface facing away from the upper surface of the bladder and a contact surface facing and in contact with the upper surface of the bladder, wherein the indicator surface faces the compression axis when the ring indicator is in the concave configuration and wherein the indicator surface faces away from the compression axis when the ring indicator is in the convex configuration. In one or more embodiments, the ring indicator comprises an indicator color that contrasts with a color of the upper surface of the bladder.

In one or more embodiments of the tissue compression devices described herein, the device further comprises a dial attached to the base, and wherein the ring indicator is attached to the dial.

In one or more embodiments of the tissue compression devices including a dial as described herein, the device further includes a plurality of dial posts extending from the top surface of the base, wherein the plurality of dial posts are arranged around a perimeter of the bladder orifice, wherein each post of the plurality of dial posts comprises an inner surface facing the bladder orifice and an outer surface facing away from the bladder orifice; wherein the dial is mounted on the plurality of dial posts, the dial comprising a dial channel that comprises an opening facing the top surface of the base, an inner wall facing the inner surfaces of the plurality of dial posts, and an outer wall facing the outer surfaces of the plurality of dial posts; mating features on the inner surface of the plurality of dial posts and the inner wall of the dial channel that are configured to move the dial towards the top surface of the base when the dial is rotated in a first direction about the compression axis and are also configured to move the dial away from the top surface of the base when rotated in a second direction about the compression axis. In one or more embodiments, the mating features comprise raised ribs on the inner surfaces of the plurality of dial posts and recesses formed into the inner wall of the dial channel, wherein the raised ribs are located within the recesses. In one or more embodiments, the dial comprises a dial orifice, and wherein the upper surface of the bladder is visible through the dial orifice. In one or more embodiments, the ring indicator comprises an indicator surface facing away from the upper surface of the bladder and a contact surface facing and in contact with the upper surface of the bladder, wherein the indicator surface faces the compression axis when the ring indicator is in the concave configuration and wherein the indicator surface faces away from the compression axis when the ring indicator is in the convex configuration, and wherein the indicator surface of the ring indicator is visible to a viewer viewing the upper surface of the bladder along the compression axis through the dial orifice when the ring indicator is in the concave configuration. In one or more embodiments, the upper surface of the bladder forms a curved surface that bulges upward away from the top surface of the base when the dial compresses the upper surface of the bladder and/or wherein the upper surface of the bladder comprises a matte finish.

In one or more embodiments of the tissue compression devices including a dial as described herein, the device further includes a stop member extending from the top surface of the base, wherein the stop member is located in the channel of the dial; a plurality of slots formed in the outer wall of the channel, wherein the stop member is configured to engage with the plurality of slots to prevent rotation of the dial about the compression axis in the absence of a force acting to move the stop member out of engagement with the plurality of stops; a stop member release lever operably connected to the stop member, wherein the stop member release lever is configured such that movement of the stop member release lever moves the stop member out of engagement with the plurality of slots in the outer wall of the dial channel such that the dial can rotate about the compression axis. In one or more embodiments, the device further comprises a second stop member extending from the top surface of the base, wherein the second stop member is located in the channel of the dial, wherein the second stop member is configured to engage with the plurality of slots to prevent rotation of the dial about the compression axis in the absence of a force acting to move the second stop member out of engagement with the plurality of stops; a second stop member release lever operably connected to the second stop member, wherein the second stop member release lever is configured such that movement of the second stop member release lever moves the second stop member out of engagement with the plurality of slots in the outer wall of the dial channel such that the dial can rotate about the compression axis.

In one or more embodiments of the tissue compression devices described herein, a first portion of the bladder including the upper surface of the bladder is located above the top surface of the base, and wherein a second portion of the bladder including the lower surface of the bladder is located between the bottom surface of the base and a limb on which the base is retained.

In one or more embodiments of the tissue compression devices described herein, the bladder comprises an upper chamber positioned adjacent a lower chamber, wherein the upper chamber is located above the top surface of the base and the lower chamber is located below the bottom surface of the base. In one or more embodiments, the bladder comprises an opening between the upper chamber and the lower chamber, wherein fluid in the upper chamber can pass into or out of the lower chamber through the opening, and wherein inflation of the bladder moves the top layer of the upper chamber away from the top surface of the base and also moves the bottom layer of the lower chamber away from the bottom surface of the base.

In one or more embodiments of the tissue compression devices including a bladder having an upper and lower chamber as described herein, an outer perimeter of the upper chamber and an outer perimeter of the lower chamber are larger than the bladder orifice as measured in a plane transverse to the compression axis.

In one or more embodiments of the tissue compression devices including a bladder having an upper and lower chamber as described herein, an outer perimeter of the upper chamber has a different shape than a shape of an outer perimeter of the lower chamber when projected onto a plane transverse to the compression axis.

In one or more embodiments of the tissue compression devices including a bladder having an upper and lower chamber as described herein, the upper chamber comprises a first upper chamber and wherein the bladder further comprises a second upper chamber located between the first upper chamber and the top surface of the base, wherein fluid within the first upper chamber passes through the second upper chamber when moving into the lower chamber.

In one or more embodiments of the tissue compression devices including a bladder having an upper and lower chamber as described herein, the lower chamber comprises a first lower chamber and wherein the bladder further comprises a second lower chamber located between the first lower chamber and the bottom surface of the base, wherein fluid within the first lower chamber passes through the second lower chamber when moving into the upper chamber.

In one or more embodiments of the tissue compression devices described herein, the bladder comprises a port in fluid communication with the bladder and configured to allow for fluid delivery into the bladder.

In one or more embodiments of the tissue compression devices described herein, the bladder comprises a pump configured to deliver fluid into the bladder.

In a second aspect, one or more embodiments of a method of monitoring pressure in a bladder of a tissue compression device as described herein may include restraining a tissue compression device over a selected location, wherein the tissue compression device comprises: a bladder comprising an upper surface located above and facing away from a top surface of a base of the tissue compression device; a ring indicator positioned above and in contact with the upper surface of the bladder, wherein the upper surface of the bladder is located between the ring indicator and the top surface of the base, and wherein the ring indicator is in a concave configuration. The method may further include increasing fluid pressure within the bladder to cause the upper surface of the bladder to apply a force to the ring indicator sufficient to move the ring indicator from the concave configuration to a convex configuration, wherein an inner edge of the indicator ring is further away from the top surface of the base when the ring indicator is in the convex configuration than when the ring indicator is in the concave configuration.

In one or more embodiments of the methods as described herein, the ring indicator is configured to move from the concave configuration to the convex configuration when the fluid pressure in the bladder reaches a selected level.

In one or more embodiments of the tissue compression devices described herein, increasing fluid pressure within the bladder comprises increasing the volume of fluid within the bladder.

In one or more embodiments of the tissue compression devices described herein, the tissue compression device comprises a dial attached to the base, and wherein the ring indicator is attached to the dial, and further wherein increasing fluid pressure within the bladder comprises rotating the dial in a first direction about an axis that extends through the upper surface of the bladder to move the dial towards the top surface of the base to compress the bladder. In one or more embodiments, the method further comprises decreasing the fluid pressure within the bladder by rotating the dial in a second direction about the axis to move the dial away from the top surface of the base.

In a third aspect, one or more embodiments of the tissue compression devices described herein may include a base and retention structure attached to the base, the retention structure configured to retain the base over selected tissue at a selected location; a bladder operably attached to the base, wherein a lower surface of the bladder faces the selected tissue when the retention structure retains the base over the selected location, and wherein an upper surface of the bladder faces away from the lower surface of the bladder; a pressure indicator positioned on the upper surface of the bladder, wherein the pressure indicator comprises: a bellowed chamber comprising a top surface that is configured to move closer to the upper surface of the bladder when pressure in the bladder is reduced and farther away from the upper surface of the bladder when pressure in the bladder is increased, and an indicator housing, wherein the bellowed chamber is located in the indicator housing and visible through the indicator housing, wherein a position of the top surface of the bellowed surface in the indicator housing is indicative of pressure in the bladder.

In one or more embodiments of the tissue compression devices described herein, the indicator housing comprises visible indicia arrayed along a side surface, wherein the visible indicia is indicative of pressure in the bladder.

In one or more embodiments of the tissue compression devices described herein, the indicator housing is attached to the upper surface of the bladder.

In one or more embodiments of the tissue compression devices described herein, the base comprises a bottom surface and a top surface, wherein the base comprises a bladder orifice formed through the base from the bottom surface to the top surface, wherein the bellowed chamber and the indicator housing of the pressure indicator are located within a perimeter of the bladder orifice. In one or more embodiments, the device defines a compression axis extending through the upper surface of the bladder, the bladder orifice in the base, and the lower surface of the bladder when the base is retained over the selected location by the retention structure, and wherein the top surface of the bellowed chamber moves along the compression axis when pressure in the bladder is reduced or increased.

In a fourth aspect, one or more embodiments of a tissue compression device as described herein may include a base and retention structure attached to the base, wherein the retention structure is configured to retain the base over selected tissue at a selected location, and wherein the base comprises a bottom surface, a top surface, and a bladder orifice formed through the base from the bottom surface to the top surface; a bladder operably attached to the base, wherein a lower surface of the bladder faces the selected tissue when the retention structure retains the base over the selected location, and wherein an upper surface of the bladder faces away from the lower surface of the bladder; and a bladder window attached to the base, wherein the bladder window is located above the bladder orifice and the upper surface of the bladder, wherein the upper surface of the bladder and the bladder window are configured such that a portion of the upper surface of the bladder contacts the bladder window when pressure in the bladder reaches a selected pressure, wherein a larger portion of the upper surface of the bladder contacts the bladder window when pressure in the bladder is increased, and wherein a smaller portion of the upper surface of the bladder contacts the bladder window when pressure in the bladder is decreased.

In one or more embodiments of the tissue compression devices described herein, the bladder window is located in a dial orifice of a dial attached to the base, wherein the dial is configured to rotate about a compression axis extending though the dial orifice, the bladder orifice, the upper surface of the bladder, and the lower surface of the bladder. In one or more embodiments, the device further comprises: a plurality of dial posts extending from the top surface of the base, wherein the plurality of dial posts are arranged around a perimeter of the bladder orifice, wherein each post of the plurality of dial posts comprises an inner surface facing the bladder orifice and an outer surface facing away from the bladder orifice; wherein the dial is mounted on the plurality of dial posts, the dial comprising a dial channel that comprises an opening facing the top surface of the base, an inner wall facing the inner surfaces of the plurality of dial posts, and an outer wall facing the outer surfaces of the plurality of dial posts; mating features on the inner surface of the plurality of dial posts and the inner wall of the dial channel that are configured to move the dial towards the top surface of the base when the dial is rotated in a first direction about the compression axis and are also configured to move the dial away from the top surface of the base when rotated in a second direction about the compression axis. In one or more embodiments, the mating features comprise raised ribs on the inner surfaces of the plurality of dial posts and recesses formed into the inner wall of the dial channel, wherein the raised ribs are located within the recesses.

In one or more embodiments of the tissue compression devices described herein, the device further comprises visible indicia indicative of the size of the portion of the upper surface of the bladder contacting the bladder window.

In one or more embodiments of the tissue compression devices described herein, an upper surface of the bladder window comprises a surface configured to reduce specular reflection from the upper surface. In one or more embodiments, the upper surface of the bladder window comprises a matte finish. In one or more embodiments, the upper surface of the bladder window comprises an anti-reflective coating. In one or more embodiments, the upper surface of the bladder window comprises a curvature configured to reduce specular reflection experienced by a view viewing the upper surface of the bladder window.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the tissue compression devices or methods described herein. Rather, a more complete understanding of the invention will become apparent and appreciated by reference to the following Description of Illustrative Embodiments and claims in view of the accompanying figures of the drawing.

BRIEF DESCRIPTION OF THE VIEWS OF THE DRAWING

FIG. 11 is a perspective view of one alternative embodiment of a tissue compression device as described herein.

DESCRIPTION OF ILLUSTRATIVE EMBODIMENTS

Figure 1:
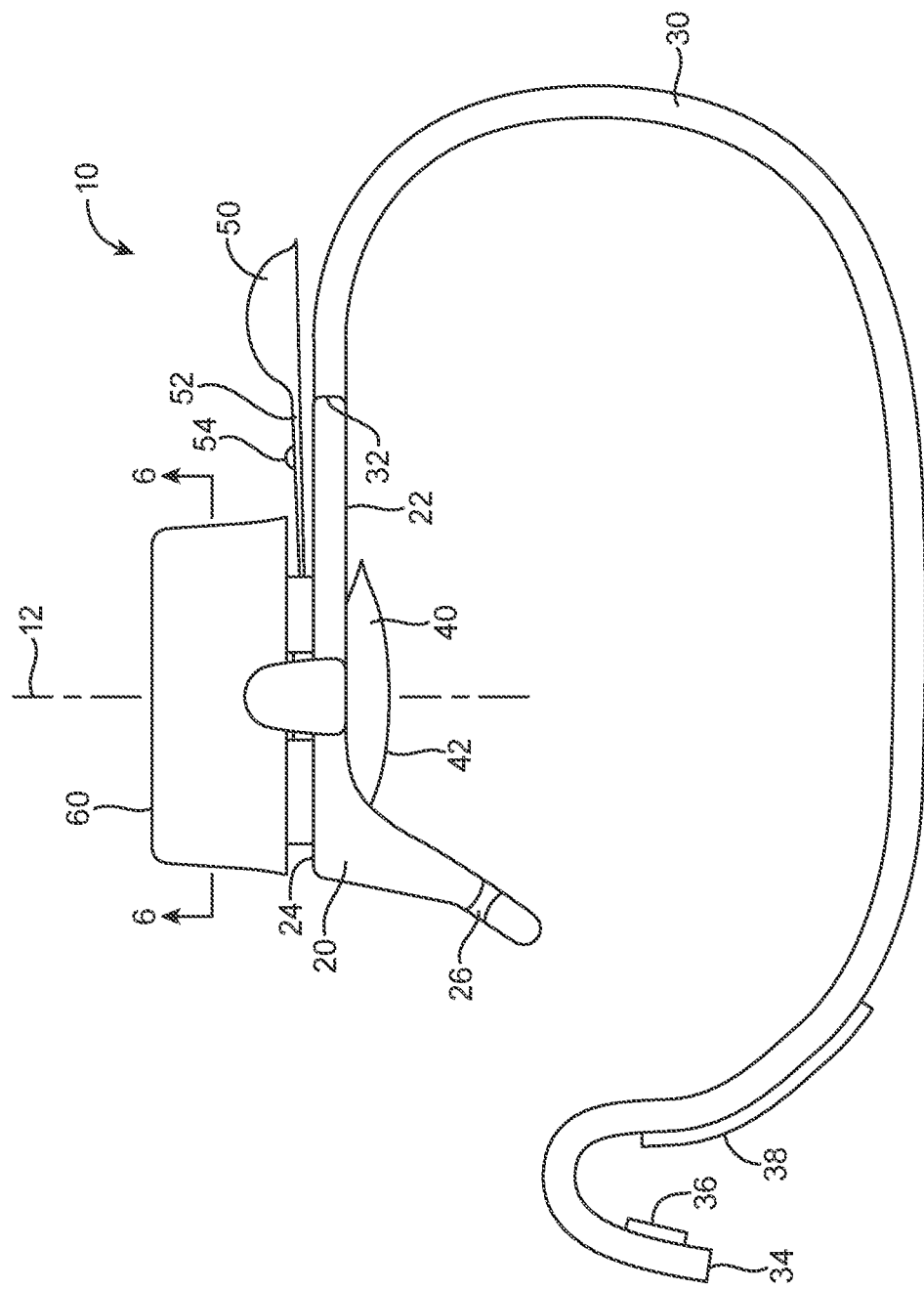
FIG. 1 is a side view of one illustrative embodiment of a tissue compression device as described herein.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

A side view of one illustrative embodiment of a tissue compression device 10 as described herein is depicted in FIG. 1. The tissue compression device 10 includes a base 20 and a retention structure 30 attached to the base 20. In the depicted embodiment, the retention structure 30 is in the form of a strap that may be configured to wrap around a limb (e.g., an arm) on or in which tissue to be compressed by the tissue compression device 10 is located. As discussed herein, in one or more embodiments the tissue compression devices described herein may be configured to compress an access site into a radial artery. The retention structure 30 includes a first end 32 attached to one end of the base 20 and an opposite free end 34. The strap of retention structure 30 also includes, in the depicted embodiment, fasteners 36 and 38 (e.g., hook and loop fasteners, interlocking mechanical fasteners, etc.) that are configured to allow the strap of retention structure 30 to be attached to a slot 26 or other opening in the base 20. The depicted form of retention structure 30 is only one example of many different straps, bands, belts, strips, etc. that could be used to secure base 20 in a selected location on a limb and in the depicted fasteners 36 and 38 are only one form of fasteners that could be used (alternatives including, e.g., buckles, snaps, etc.).

In one or more embodiments, the retention structure 30 may be inextensible when secured around a limb or other anatomical structure such that increasing pressure in the bladder 40 of a tissue compression device as described herein does not merely result in elongation or stretching of the retention structure 30 rather than increasing pressure on, e.g., an access site. In one or more alternative embodiments, such as the illustrative embodiments depicted in FIGS. 23-27, the tissue compression devices described herein may include a strap retainer that is elastically attached to the base of the tissue compression device and which may, optionally, include a tension indicator that may, in one or more embodiments, limit travel distance between the strap retainer and the base of the tissue compression device.

The base 20 of the tissue compression device 10 includes a bottom surface 22 and a top surface 24. The bottom surface 22 of the base 20 is configured to face a limb when retained thereon by the retention structure 30. The top surface 24 of the base 20 faces away from the limb on which the tissue compression device 10 is located. Other features of the base 20 of the tissue compression device 10 will be described in more detail with respect to the following figures.

Also depicted in connection with the illustrative embodiment of FIG. 1 is a bladder 40, although in the view of FIG. 1 only a portion of the bladder 40 is visible. In particular, the lower surface 42 of the bladder 40 is seen in FIG. 1. Inflation of the bladder 40 will, in one or more embodiments, tend to move the lower surface 42 of the bladder 40 away from the bottom surface 22 of the base 20. When the base 20 is restrained on a limb by, e.g., the retention structure 30, inflation of the bladder 40 will force the lower surface 42 of the bladder 40 against the skin of the patient and, thereby, provide compression of selected tissue (e.g., tissue at an access site, etc.) in contact with the lower surface 42 of the bladder 40. That compression, when applied at an access site can, in one or more embodiments, provide hemostasis.

Another feature depicted in connection with the illustrative embodiment of tissue compression device 10 is a pump 50 that is fluidly connected to the bladder 40 through a channel 52. In one or more embodiments, a release valve 54 may be provided to allow for deflation of the bladder 40. Although depicted as being located within the channel 52, in one or more alternative embodiments the release valve 54 may be provided elsewhere in the tissue compression device 10.

As described herein, the volume of the bladder 40 may be increased (e.g., inflated) to increase pressure exerted on a selected location on a patient. Pump 50 is only one example of a fluid delivery device that can be used to deliver fluid to the bladder 40. Pumps used to deliver fluid to bladders in tissue compression devices described herein may take many different forms, only one of which is depicted in connection with the embodiment of tissue compression device 10 depicted in FIG. 1.

Although the illustrative embodiment of tissue compression device 10 includes a fluid delivery device in the form of a pump 50 that is integrally formed with the bladder 40, in one or more alternative embodiments, fluid may be delivered to the bladder 40 using any suitable fluid delivery device. For example, the volume of fluid in the bladder 40 may be increased (or, in some instances, decreased) using a syringe inserted into a port provided in the bladder 40. In one or more other embodiments, the bladder 40 may be provided with a fixed volume of a fluid (e.g., air, saline, etc.) with changes in the compression force being provided to a patient using the dial 60 as will be described further herein. In other words, the tissue compression devices described herein may or may not include a pump or other fluid delivery device to inflate or otherwise deliver fluid into the bladder 40.

Whether or not the bladders of tissue compression devices described herein are inflated or have a fixed volume, dial 60, which is attached to the base 20 above the top surface 24, may be used to increase and/or decrease the amount of compression delivered by the tissue compression device 10 described herein. In particular, the dial 60 may be rotated about a compression axis 12 to increase or decrease the compression provided by the bladder 40. Specific details with respect to the mechanism by which rotation of dial 60 may be used to increase or decrease compression will be described further herein.

Figure 3:
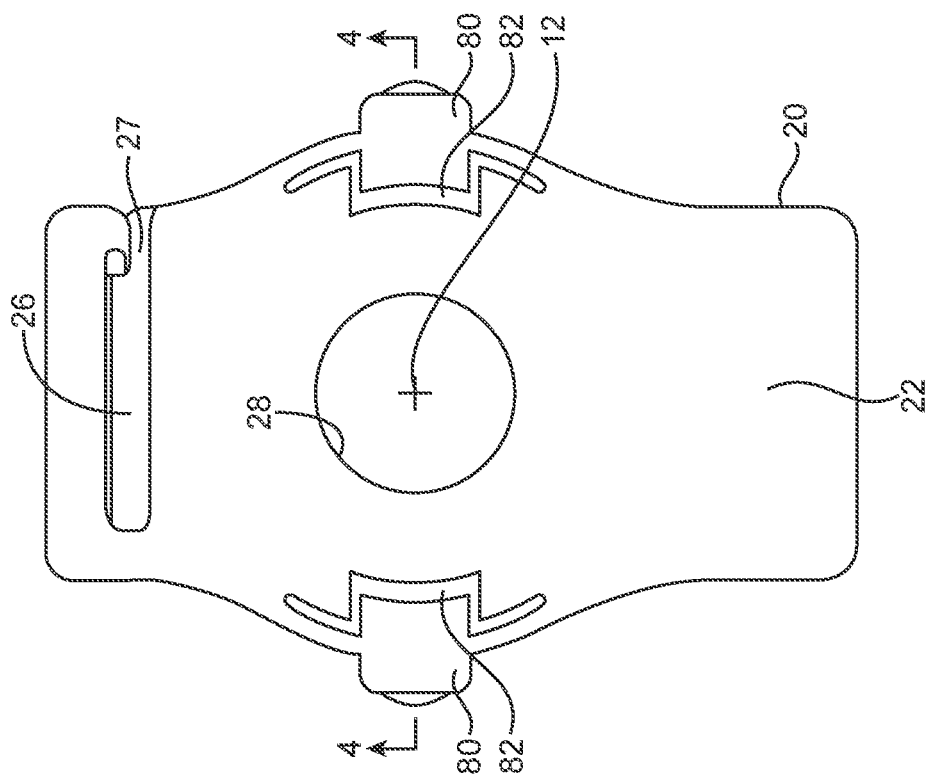
FIG. 3 is a bottom view of the tissue compression device depicted in FIG. 1, with the tension structure and the bladder removed from the view for clarity.
Figure 2:
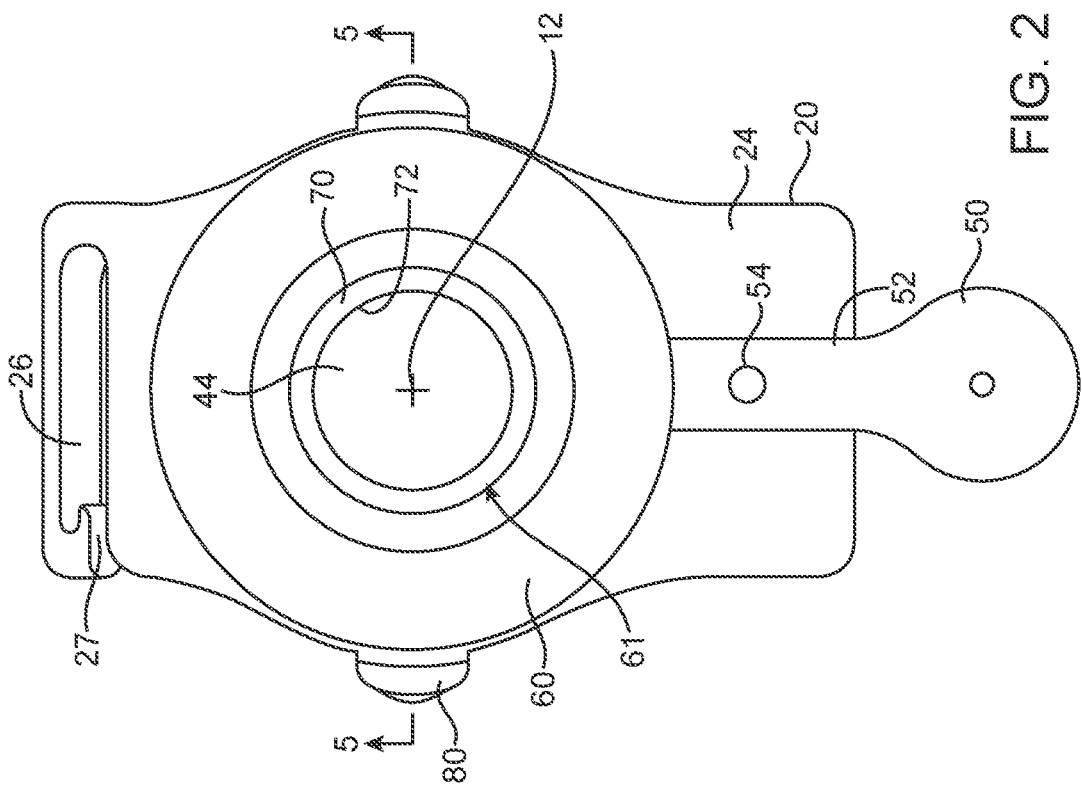
FIG. 2 is a top view of the tissue compression device depicted in FIG. 1, with the tension structure (e.g., the strap in this illustrative embodiment) removed from the view for clarity.

FIG. 2 is a top view of tissue compression device 10 as depicted in FIG. 1 with the retention structure (e.g., strap) 30 removed for clarity. Only the top surface 24 of the base 20 is visible in FIG. 2, although an additional feature more clearly seen in FIG. 3 is the opening 27 into slot 26. That opening 27 allows a strap to slide into the slot 26 through the opening 27 during placement of the tissue compression device 10. As a result, the opening 27 may simplify attachment of the strap of retention structure 30 because the end of the strap need not be threaded through a hole in the base 20 in order to secure it.

Among the other features depicted in FIG. 2 are the dial orifice 61 which is an opening through the dial 60. The dial orifice 61 provides, in one or more embodiments, visible access to the upper surface 44 of the bladder 40. The upper surface 44 of the bladder 40 faces away from the lower surface 42 of the bladder 40. Also visible within the dial orifice 61 in the depicted embodiment of tissue compression device 10 is the ring indicator 70 with its inner edge 72 being located closest to the compression axis 12. The ring indicator 70, as will be described in more detail below, can operate to provide an indication regarding the level of compression provided by the tissue compression device 10. Additional features depicted in FIG. 2 include stop member release levers 80 which, as will be described in more detail below, can be used to release the dial 60 for rotation about compression axis 12.

FIG. 3 is a view of the bottom surface 22 of the base 20 in which the bladder 40 has been removed from the base 20 to expose additional features of the tissue compression device as described herein. Among the features seen in FIG. 3 are the compression axis 12, bottom surface 22 of the base 20, and the bladder orifice 28 which is provided in the base 20. In one or more embodiments, the bladder orifice 28 is formed through the base 20 from the bottom surface 22 to the top surface 24 and, as will be described further herein, the bladder orifice 28 can, in one or more embodiments, be used to retain the bladder 40 in engagement with the tissue compression device 10.

As can be seen by the combination of FIGS. 1-3, the compression axis 12 defined by the illustrative embodiment of tissue compression device 10 extends through the upper surface 44 of the bladder 40, the bladder orifice 28 in the base 20 and the lower surface 42 of the bladder 40 when the base 20 is retained over selected tissue (on, e.g., a limb) by the retention structure 30.

Another feature that can be seen with reference to the view in FIG. 3 of the illustrative embodiment of tissue compression device 10 are the stop member release lever relief openings 82 that may be provided in the base 20 to allow movement of the stop member release levers 80 towards the compression axis 12. Movement of the stop member release levers 80 may, as will be described further herein, be used to allow rotation of the dial 60 about the compression axis 12 to provide for increases or decreases in the compression provided by the tissue compression devices described herein.

Figure 4:
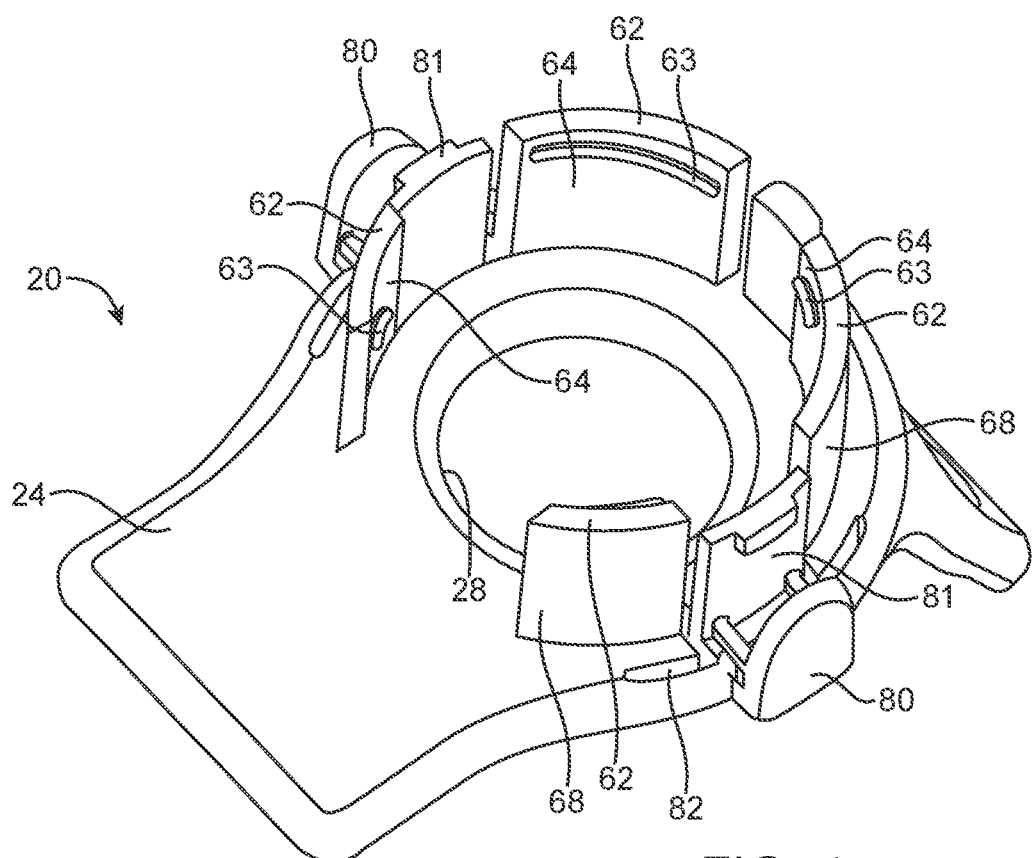
FIG. 4 is a perspective view of the base of the tissue compression device of FIG. 1 with the dial removed.
Figure 6:
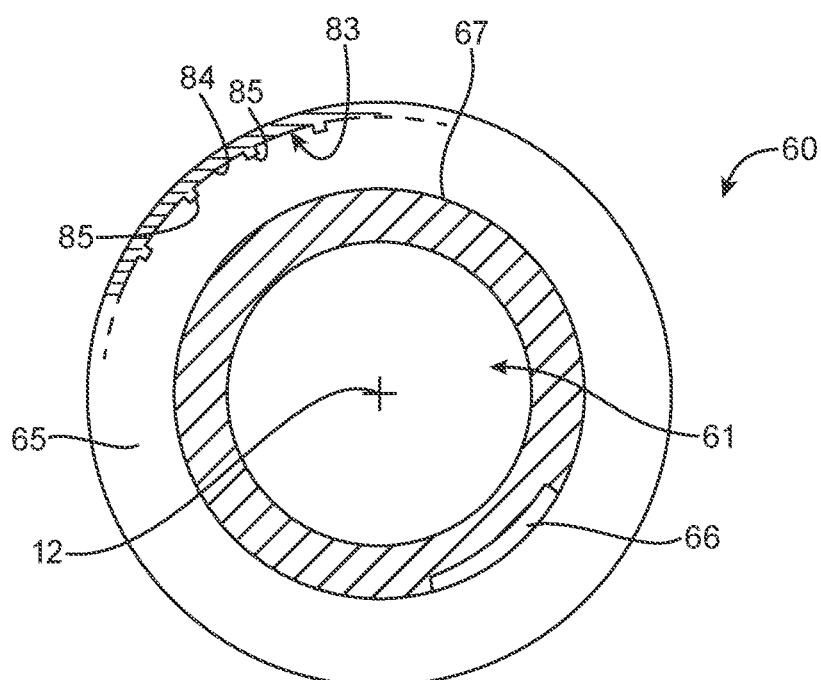
FIG. 6 is a cross-sectional view of the dial of the illustrative embodiment of a tissue compression device as depicted in FIG. 1, with the cross-sectional view taken along line 6-6 in FIG. 1.
Figure 5:
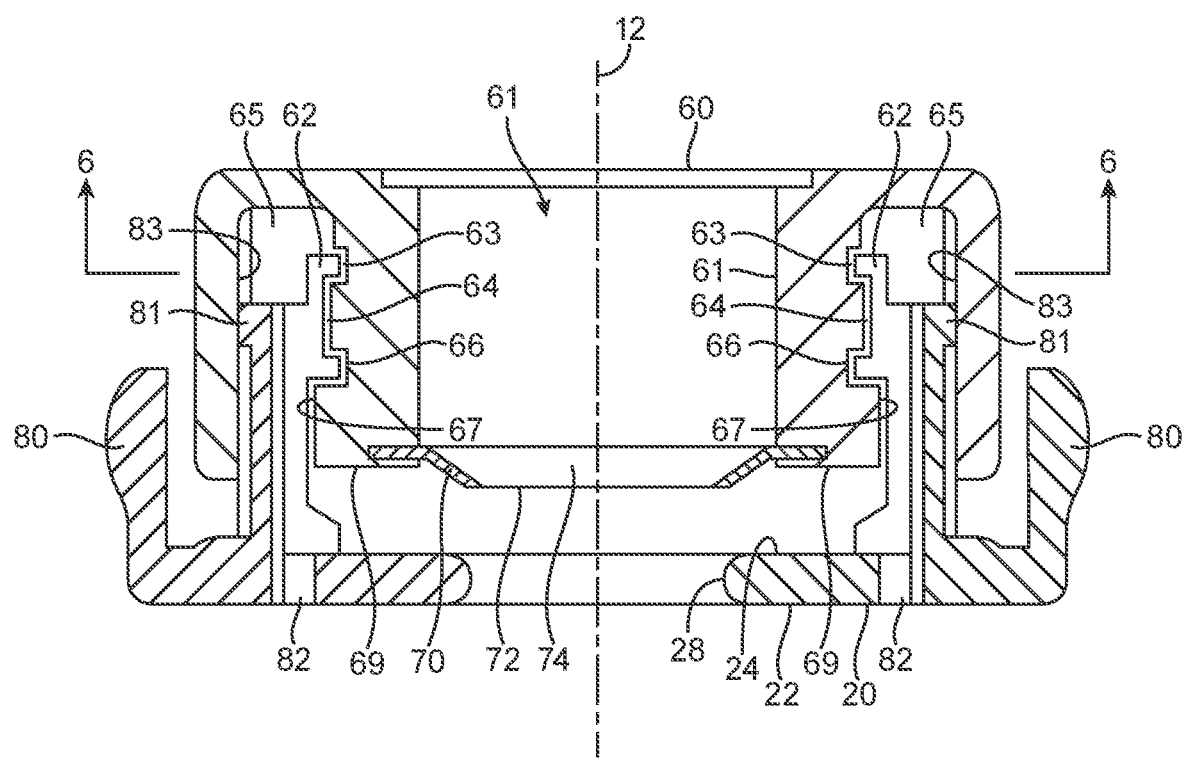
FIG. 5 is a cross-sectional view of the tissue compression device depicted in FIG. 3, with the cross-sectional view being taken along line 5-5 in FIG. 3 (and with the bladder being removed for clarity).

Operation of the dial 60 on the base 20 of the tissue compression device 10 in the illustrative embodiment of tissue compression device 10 as depicted in FIGS. 1-3 will now be described with reference to FIGS. 4-6. In particular, FIG. 4 is a perspective view of the base 20 of the illustrative embodiment of a tissue compression device 10 with the bladder 40, dial 60, and retention structure 30 removed from the base 20. FIG. 5 is a cross-sectional view of the base 20 of the illustrative embodiment of tissue compression device 10 taken along line 5-5 in FIG. 3. FIG. 6 is a cross-sectional view of the dial 60 removed from the remainder of the tissue compression device 10 (with the view being taken along line 6-6 in FIG. 1).

As seen in the other figures described above, the base 20 includes a top surface 24. Other features seen in the views of FIGS. 1-3 include, for example, the stop member release levers 80 along with one of the stop member release lever relief openings 82.

Among the features are not seen in the previously described figures are the stop members 81 that are operably connected to the stop member release levers 80. Movement of each of the stop member release levers 80 inwardly toward the compression axis 12 moves the connected stop member 81 inwardly toward the compression axis 12. As described in more detail below, inward movement of the stop members 81 allows for rotation of the dial 60 about the compression axis 12.

Other features not seen in the views of FIGS. 1-3 include the dial posts 62 that extend from the top surface 24 of the base 20. In one or more embodiments the dial posts 62 are arranged around a perimeter of the bladder orifice 28 formed through the base 20. In the depicted embodiment, four dial posts 62 are depicted, although any number of dial posts 62 could be provided so long as they function to retain the dial 60 on the tissue compression device 10 and provide for its rotation about the compression axis 12. In one or more embodiments, each of the stop members 81 may be located between a pair of dial posts 62. Such an arrangement may, in one or more embodiments, provide additional support and control for proper operation of the stop members 81 with respect to the dial 60 of the tissue compression device 10.

The dial 60 includes a dial channel 65 that includes an opening facing the top surface 24 of the base 20, with the dial posts 62 being located in the dial channel 65. The dial channel 65 includes an inner wall facing the inner surfaces 64 of the dial posts 62 and an outer wall 84 facing the outer surfaces 68 of the dial posts 62.

The dial posts 62 may, in one or more embodiments such as the depicted embodiment, include raised ribs 63 that extend from the inner surfaces 64 of the dial posts 62. The raised ribs 63 may be arranged in a helical manner on the inner surfaces 64 of the dial posts 62. Further, the raised ribs 63 may fit within the recesses 66 formed into the inner wall 67 of the dial channel 65. The raised ribs 63 and the recesses 66 cooperate and are configured to move the dial 60 towards the top surface 24 of the base 20 when the dial 60 is rotated in a first direction about the compression axis 12.

Movement of the dial 60 towards the top surface 24 of the base 20 may, as described herein, result in an increase in pressure within the bladder 40. The pressure within the bladder 40 increases because the dial 60 compresses the portion of the bladder located between the dial 60 and the top surface 24 of the base 20. In one or more embodiments, movement of the dial 60 towards the top surface 24 of the base 20 moves the bottom surface 69 of the dial 60 (see, e.g., FIGS. 5, 7 and 8) towards the top surface 24 of the base 20.

As the bottom surface 69 moves towards the top surface 24 of the base 20, the bottom surface 69 presses against the upper surface 44 of the bladder 40 to compress the bladder 40 between the bottom surface 69 of the dial 60 and the top surface 24 of the base 20. In embodiments that include features such as, e.g., an indicator ring 70 at or near the bottom surface 69 of the dial 60, those features (such as the indicator ring 70) may also act on the upper surface 44 of the bladder 40 to compress the bladder 40 as the dial 60 moves towards the upper surface 24 of the base 20.

As the bladder 40 is compressed between the bottom surface 69 of the dial and the top surface 24 of the base 20 (and other features such as, e.g., the indicator ring 70), the upper surface 44 of the bladder 40 may, in one or more embodiments, conform to the shape of the bottom surface 69 of the dial 60 (and other features such as, e.g., the indicator ring 70)—particularly in those embodiments in which the upper surface 44 of the bladder 40 is flexible. In one or more alternative embodiments in which the upper surface 44 of the bladder 40 is less flexible, the upper surface 44 may or may not conform to the features found at or near the bottom of the dial 60. In the one or more embodiments in which the upper surface 44 of the bladder 40 is flexible, however, the upper surface 44 of the bladder 40 may bulge or extend slightly upward into the dial opening 61 (and, if present, the opening formed within the indicator ring 70).

The raised ribs 63 and the recesses 66 may further be configured to move the dial 60 away from the top surface 24 of the base 20 when the dial 60 is rotated in in an opposite direction about the compression axis 12. Movement of the dial 60 away from the top surface 24 of the base 20 may, as described herein result in a decrease in pressure within the bladder 40. Pressure within the bladder 40 decreases as the dial 60 moves away from the top surface 24 of the base 20 because movement of the dial 60 in that direction allows the portion of the bladder 40 located between the dial 60 and the top surface 24 of the base 20 to expand in volume. In one or more embodiments, movement of the dial 60 away from the top surface 24 of the base 20 moves the bottom surface 69 of the dial 60 (see, e.g., FIGS. 5, 7 and 8) away from the top surface 24 of the base 20.

The raised ribs 63 and recesses 66 are merely one example of mating features that may be provided on the dial posts 62 and in the dial channel 65 to provide for movement of the dial 60 towards and away from the top surface 24 of the base 20 when the dial 60 is rotated about compression axis 12. Other complementary structures in or on the dial posts and in the dial channel may be used to move the dial 60 towards or away from the top surface 24 of the base 20 to increase or decrease pressure within a bladder 40.

Rotation of the dial 60 about the compression axis may, in one or more embodiments such as the illustrative embodiment depicted in FIGS. 1-6 and/or 11-17, be limited or prevented by features also provided in the tissue compression devices described herein. In one or more embodiments, rotation of the dial 60 about the compression axis 12 may be limited in both directions. In other words, the dial 60 may be prevented from rotation in one direction that would move the dial 60 closer to the top surface 24 of the base 20, as well as rotation in the opposite direction that would move the dial away from the top surface 24 of the base 20.

In the illustrative embodiment of tissue compression device 10, the structures that prevent rotation of the dial 60 include stop members 81 which, as described above, are attached to stop member release levers 80. Because the stop members 81 themselves are located within the dial channel 65 when the tissue compression device 10 is assembled, a user manipulates the stop member release levers 80 to move the stop members 81 because the stop member release levers 80 are accessible. As described herein, movement of the stop members 81 allows for rotation of the dial 60 about the compression axis 12.

The stop members 81 prevent rotation of the dial 60 about compression axis 12 because the stop members 81 are configured to engage with slots 84 that are provided in the outer wall 83 of the dial channel 65. In particular, the slots 84 are bounded on each side by raised portions 85. Each stop member 81 fits within one or more of the slots 84 and rotation of the dial 60 about axis 12 is limited and/or prevented by the raised portions 85 found on each side of the slot 84. Although not depicted in FIG. 6, in one or more embodiments, the entire perimeter of the outer wall 83 of the dial channel 65 includes slots 84 bounded by raised portions 85 so that, regardless of the particular rotational orientation of the dial 60 on the base 20, the stop members 81 may engage with at least one slot 84 in the dial 62 control rotation of the dial 60 about compression axis 12.

As discussed herein, the stop member release levers 80 are operably connected to the stop members 81. The stop member release levers 80 are configured such that movement of the stop member release lever 80 moves its associated stop member 81 out of engagement with, in the depicted embodiment, the slots 84 in the outer wall 83 of the dial channel 65. In a design such as that depicted in the illustrative embodiment of FIGS. 1-6, releasing only one of the stop members 81 from a slot 84 in the outer wall 83 of the dial channel 65 may not allow rotation of the dial 60 about the compression axis 12. Rather, in a design such as that depicted in the illustrative embodiment of FIGS. 1-6, rotation of the dial 60 about the compression axis 12 may require that both of the stop member release levers 80 be used to move their attached stop members 81 out of engagement with slots 84 in the outer wall 83 of the dial channel 65.

One potential advantage of such a design is that rotation of the dial 60 about compression axis 12 may require the use of two hands, e.g., the thumb and a finger on one hand to move the stop member release levers 80 and their associated stop members 81 out of engagement with the slots 84 in the dial channel 65 and a second hand to rotate the dial 60 about the compression axis 12. As a result, a patient wearing the tissue compression device 10 on, e.g., an arm, would not typically be able to rotate the dial 60 to adjust the compression provided by the device 10 themselves because the hand of the limb on which the tissue compression device 10 is located will not be able to reach the dial 60 and/or the stop member release levers 80. In other words, requiring compression of the stop member release levers using a thumb and finger to move associated stop members that limit or prevent rotation of dial 60 in both directions about axis 12 may provide a tissue compression device in which the pressure cannot readily be adjusted by a patient wearing the device on an arm.

Although the stop member release levers 80, stop members 81, and the slots 84 with raised portions 85 on the outer wall 83 of the dial channel provide one embodiment of structures that can be used to prevent rotation of a dial on a tissue compression device as described herein, many other structures may also be used to prevent rotation in both directions about a compression axis as described herein.

The tissue compression devices described herein may, in one or more embodiments, include a pressure indicator to provide visual feedback regarding the amount of compression being delivered by the tissue compression devices described herein. In one or more embodiments of tissue compression devices as described herein, such as the illustrative embodiment depicted in FIGS. 1-6, the tissue compression device 10 includes a pressure indicator in the form of a ring indicator 70 that is attached to the dial 60 so that it is positioned above and in contact with the upper surface 44 of the bladder 40.

Figure 7:
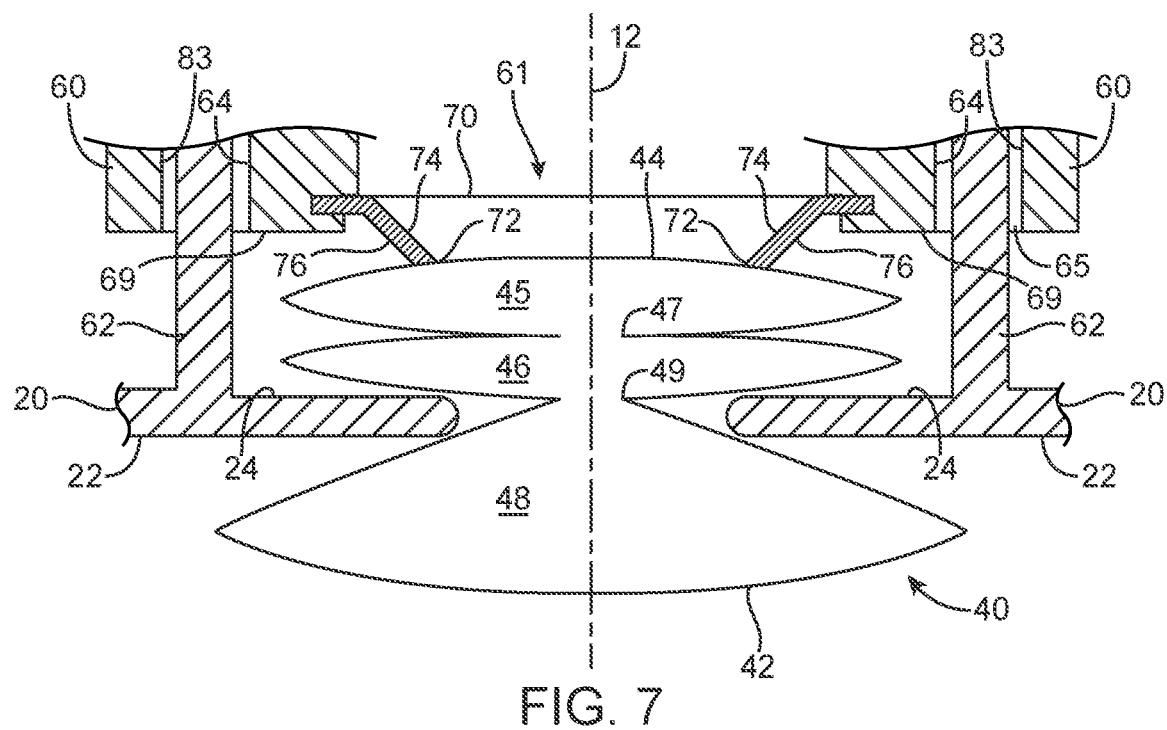
FIG. 7 is an enlarged cross-sectional view of the bladder located within the base of a tissue compression device of FIG. 5, with the ring indicator in a concave configuration.
Figure 8:
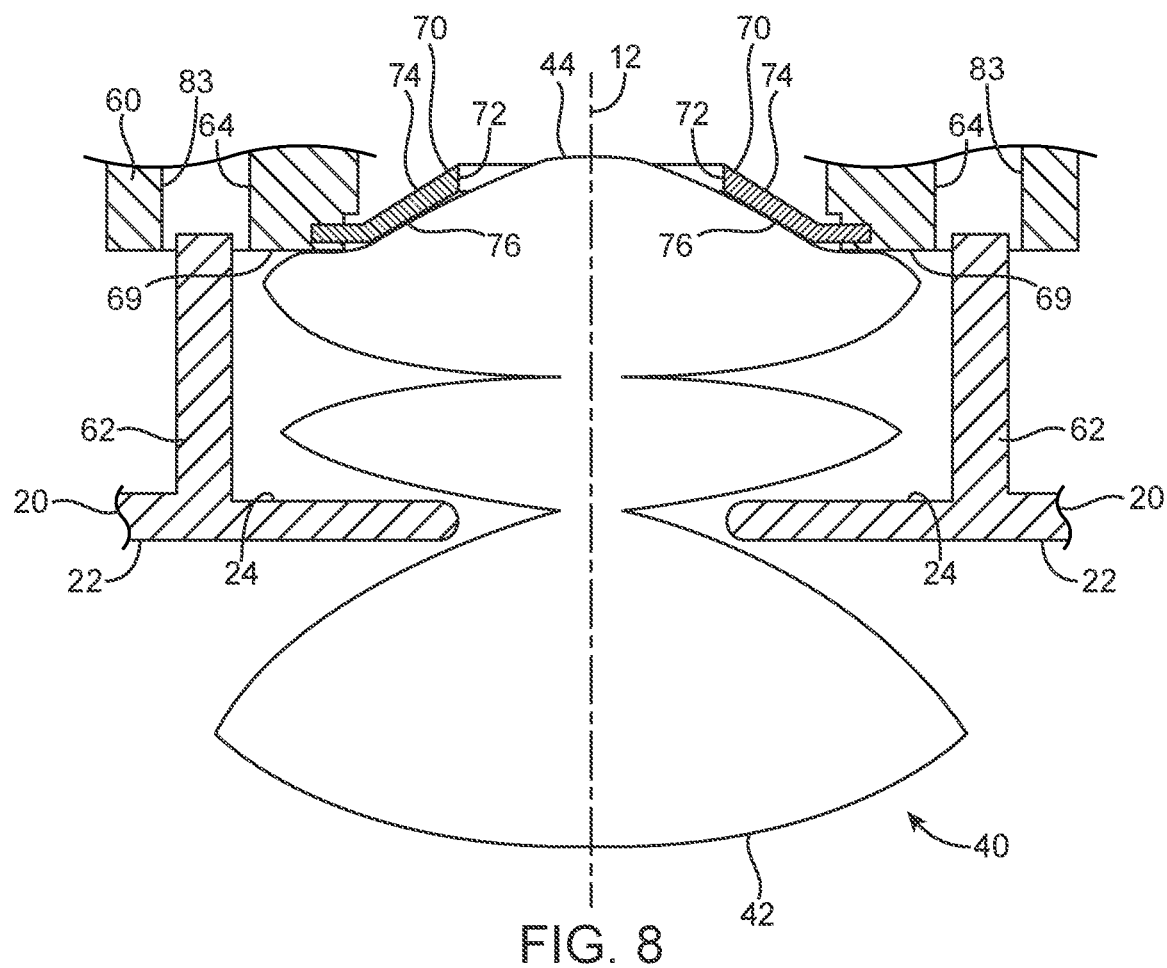
FIG. 8 is an alternative view of the bladder depicted in FIG. 7, with the bladder inflated and the ring indicator in its convex configuration.

In the illustrative embodiment depicted in FIGS. 7-8, the ring indicator 70 has a concave configuration and a convex configuration. In the concave configuration as depicted in FIG. 7, an inner edge 72 of the indicator ring 70 is located closer to the top surface 24 of the base 20. In its convex configuration as depicted in FIG. 8, the inner edge 72 of the indicator ring 70 is located further away from the top surface 24 of the base 20.

The indicator ring 70 moves between the concave configuration and the convex configuration based on the force exerted on the indicator ring 70 by the upper surface 44 of the bladder 40. The force exerted on the indicator ring 70 by the upper surface 44 of the bladder 40 is a function of the fluid pressure within the bladder 40. Increasing the fluid pressure within the bladder 40 (and, as a result, increasing the force exerted on the indicator ring 70 by the bladder 40) can be accomplished by delivering additional fluid into the bladder 40 and/or by moving the dial 60 to compress the bladder 40 between the top surface 24 of the base 20 and the dial 60 while holding the amount of fluid within the bladder 40 constant. Conversely, decreasing the fluid pressure within the bladder 40 (and, as a result, decreasing the force exerted on the indicator ring 70 by the bladder 40) can be accomplished by removing fluid from the bladder 40 and/or by moving the dial 60 away from the top surface 24 of the base 20 to allow the bladder 40 expand while holding the amount of fluid within the bladder 40 constant.

As the bottom surface 69 moves towards the top surface 24 of the base 20 during compression of the bladder 40 by the dial 60, the bottom surface 69 presses against the upper surface 44 of the bladder 40 to compress the bladder 40 between the bottom surface 69 of the dial 60 and the top surface 24 of the base 20. In the embodiment depicted in FIGS. 7-8, indicator ring 70 at or near the bottom surface 69 of the dial 60 also acts on the upper surface 44 of the bladder 40 to compress the bladder 40 as the dial 60 moves towards the upper surface 24 of the base 20.

As the bladder 40 is compressed between the bottom surface 69 (and the indicator ring 70) and the top surface 24 of the base 20, the upper surface 44 of the bladder 40 may, in one or more embodiments, conform to the shape of the bottom surface 69 of the dial 60 and the indicator ring 70—particularly in those embodiments in which the upper surface 44 of the bladder 40 is flexible. In one or more alternative embodiments in which the upper surface 44 of the bladder 40 is less flexible, the upper surface 44 may or may not conform to the features found at or near the bottom of the dial 60.

In the one or more embodiments in which the upper surface 44 of the bladder 40 is flexible, however, the upper surface 44 of the bladder 40 may bulge or extend slightly upward away from the top surface 22 of the base 20 and into the dial opening 61 and the opening formed within the inner edge 72 of the indicator ring 70. This bulging or curvature may typically occur when, e.g., the dial 60 compresses the upper chamber 45 of the bladder 40.

Specular reflection (e.g., glare) from the upper surface of a bladder may, in one or more embodiments, prevent or limit viewing of the tissue located beneath the bladder. To limit specular reflection, one or more features may be provided in the tissue compression devices described herein. One optional feature that may be provided in one or more embodiments of the tissue compression devices described herein is depicted in connection with FIG. 8. In particular, the bulge or curvature of the upper surface 44 of the bladder 40 within the opening formed by the inner edge 72 of the indicator ring 70 (or the dial orifice 61 in the dial 60 in those embodiments in which an indicator ring is not provided) may, in one or more embodiments, provide an advantage in that specular reflection from the upper surface 44 of the bladder 40 may be reduced because of the curvature of that surface.

In one or more alternative embodiments, the upper surface 44 of the bladder 40 may be provided with a matte finish, anti-reflective coating, etc. that is configured to reduce specular reflection from the upper surface 44 of the bladder 40. In one or more embodiments, any matte finish, anti-reflective coating, etc. provided on the upper surface 44 of the bladder 40 may reduce specular reflection from the upper surface 44 of the bladder of visible light by 50% or more (when the upper surface 44 of the bladder 40 is provided in a planar or flat configuration). Any such matte finish, anti-reflective coating, etc. should, however, be selected such that viewing of the tissue beneath the bladder 40 is not unduly hindered.

In one or more embodiments, the ring indicator 70 can be described as a bi-stable structure in which the ring indicator 70 will only be found in either the convex or concave configurations (in the absence of any force that would constrain it in between those configurations).

In one or more of the bi-stable embodiments, the ring indicator 70 is configured to move from the concave configuration to the convex configuration when the force exerted by the bladder 40 on the ring indicator 70 reaches (or exceeds) a selected force. The selected force exerted by the bladder 40 on the ring indicator 70 may, in one or more embodiments, be correlated to the compression force being delivered by the lower surface 42 of the bladder 40 at a selected location on a patient.

Referring now to FIGS. 7-8, enlarged views of a portion of the base 20 including the bladder orifice 28, a bladder 40 retained therein, and dial 60 with ring indicator 70 are provided to more completely describe operation of the dial 60 and ring indicator 70 in connection with the tissue compression devices described herein. The ring indicator 70 is depicted in its concave configuration in FIG. 7 and in its convex configuration in FIG. 8. As discussed herein, movement of the ring indicator 70 from the concave configuration to the convex configuration is caused by forces exerted on the ring indicator 70 by the upper surface 44 of the bladder 40.

The ring indicator 70 includes an indicator surface 74 that faces away from the upper surface 44 of the bladder 40 and a contact surface 76 that faces the upper surface 44 of the bladder 40. Although the upper surface 44 of the bladder 40 may not be in contact with the contact surface 76 of the ring indicator 70 while the ring indicator 70 remains in its concave configuration (see, e.g., FIG. 7), the upper surface 44 of the bladder 40 will, in most embodiments, be in contact with the contact surface 76 of the ring indicator 70 at some point during its movement from the concave configuration to the convex configuration (see, e.g., FIG. 8).

In one or more embodiments, the indicator surface 74 of the ring indicator 70 may be described as facing the compression axis 12 when the ring indicator 70 is in its concave configuration (see, e.g., FIG. 7) and the indicator surface 74 of the ring indicator 70 may be described as facing away from the compression axis 12 when the ring indicator 70 is in its convex configuration.

In one or more embodiments, the indicator surface 74 of the ring indicator 70 may include one or more indicator colors that contrast with one or more of: the color of the upper surface 44 of the bladder 40, the interior of the dial orifice 61, and the top surface 24 of the base 20. The one or more indicator colors used on the indicator surface 74 may be useful for improving visibility of the indicator surface 74 of the ring indicator 70 when the ring indicator 70 is in its concave configuration. Potentially useful indicator colors may include but are not limited to, e.g., red, yellow, orange, green, a series of colors (such as, e.g., a rainbow-like arrangement), etc.

In addition to providing visible indication of the status of the ring indicator 70, movement of the ring indicator 70 from the concave configuration to the convex configuration may, in one or more embodiments, also be accompanied by an audible indication. For example, the ring indicator 70 may make a sound such as a click, pop, etc. when moving from the concave configuration to the convex configuration to provide an audible indication that the selected pressure level in the bladder has been reached.

As discussed herein, movement of the ring indicator 70 from its concave configuration to its convex configuration occurs, in one or more embodiments, when the pressure within the bladder 40 increases so that the bladder 40 exerts a force that meets or exceeds a selected force. The pressure within the bladder 40 is, in one or more embodiments, controlled by the volume of air or other fluid in the bladder 40 as well as the position of the bladder 40 relative to the skin of a patient on which the tissue compression device containing the bladder 40 is retained (because lower surface 42 of the bladder 40 is in contact with the patient's skin).

As described herein, the indicator surface 74 is visible to a user viewing the upper surface 44 of the bladder 40 through the dial orifice 61 when the indicator ring 70 is in the concave configuration. In contrast, the indicator surface 74 of the indicator ring 70 is obscured by the dial 60 and, as a result, is not easily or readily viewable by a user viewing the upper surface 44 of the bladder 40 through the dial orifice when the ring indicator 70 is in its convex configuration. As a result, the movement of indicator ring 70 from the concave configuration to the convex configuration in which the indicator surface 74 is not easily or readily visible to a user viewing the upper surface 44 of the bladder 40 through the dial orifice 61 may provide, in one or more embodiments, a visible indicator that the pressure within the bladder 40 has reached or exceeded a selected level.

Once the pressure in the bladder 40 has reached the selected level so that the indicator ring 70 moves from the concave configuration to the convex configuration, a user may rotate the dial 60 to further adjust the pressure within the bladder 40 by moving the dial 60 towards or away from the upper surface 24 of the base 20. Moving the dial 60 towards or away from the upper surface 24 of the base 20 may, in one or more embodiments, result in compression of the upper chamber of the bladder 40, with that compression changing the pressure applied to the patient by the tissue compression device. As described herein, movement of the dial 60 towards or away from the upper surface 24 of the base 20 may be accomplished by mating features located on the dial posts 62 which are located in the dial channel 65 defined between an inner surface 64 and outer surface 83 as described above in connection with, e.g., FIGS. 4-6.

In one or more embodiments, the dial 60 and/or base 20 may include indicia (e.g., alphanumeric characters, gradation marks, etc.) such that the relative rotational position of the dial 60 on the base 20 can be visually discerned. That relative rotational position may be correlated to selected changes in the compression of the bladder located in the tissue compression devices described herein. For example, rotation of the dial 60 about the axis 12 by a selected number of degrees (e.g., 15 degrees, 20 degrees, 30 degrees, etc.) may correlate to a selected vertical distance (along, e.g., axis 12) over which the dial 60 moves towards or away from the base 20. That selected vertical distance may, in one or more embodiments, correlate to a selected change in the fluid pressure in the bladder 40. As a result, rotation of the dial 60 about the axis 12 by a selected number of degrees (which can be visually discerned by a user when indicia are provided on the dial and/or base) may, in one or more embodiments, be correlated to a selected change in pressure in the bladder 40.

Although the indicator rings used in tissue compression devices as described herein may, in one or more embodiments, be provided in the form of bi-stable devices as described above, in one or more alternative embodiments, the ring indicators may not be the form of bi-stable devices. For example, the indicator ring 70 may be constructed so that it can move in a more continuous manner between the concave configuration depicted in FIG. 7 and the convex configuration depicted in FIG. 8. In one or more of such embodiments, the inner edge 72 of the indicator ring 70 may be found at any position between the concave configuration and the convex configuration depending on the fluid pressure found in the bladder 40.

As described above, the fluid pressure in the bladder 40 corresponds to the force exerted on the indicator ring 70 by the upper surface 44 of the bladder 40. As a result, as the fluid pressure in the bladder 40 increases, the location of the inner edge 72 of the indicator ring 70 may move in a corresponding and continuous manner from its location in the concave configuration to its location in the convex configuration as the force exerted by the upper surface 44 of the bladder 40 on the indicator ring 70 increases. If the indicator surface 74 includes one or more colors (in, e.g., a rainbow-like array, etc.), the color or colors visible (or at least predominantly visible) to a user through the dial opening 61 may change as the indicator ring 70 moves from the concave configuration to the convex configuration.

In the one or more embodiments in which the indicator ring 70 is not a bi-stable device, the indicator ring 70 may, however, be biased such that it takes the concave configuration as depicted in FIG. 7 in the absence of any external forces applied to move the indicator ring out of that concave configuration.

The illustrative embodiment of bladder 40 depicted in, e.g., FIGS. 7-8, includes multiple chambers 45, 46, and 48. The upper chambers 45 and 46 are located between the upper surface 24 of the base 20 and the ring indicator 70 along with the bottom of the dial 60. The lower chamber 48 is positioned below the base 20. The two upper chambers 45 and 46 are in fluid communication with each other through an opening 47, while the chambers 46 and 48 are in fluid communication with each other through an opening 49. The upper chamber 45 includes a top layer that defines the upper surface 44 of the bladder 40, while the lower chamber 48 includes a bottom layer that defines the lower surface 42 of the bladder 40.

Although the depicted embodiment of bladder 40 includes two upper chambers above the upper surface 24 of the base 20 and only one lower chamber below the bottom surface 22 of the base 20, alternative embodiments of the tissue compression devices described herein that include bladders with multiple chambers may include any number of upper chambers above the upper surface 24 of the base 20 (including, e.g., as few as one upper chamber). Similarly, alternative embodiments of the tissue compression devices described herein may include bladders having any number of lower chambers below the bottom surface 22 of the base 20 (including, e.g., two or more lower chambers). Many different bladders may be used in the tissue compression devices described herein. The bladder 40 depicted and described in connection with the illustrative embodiment of tissue compression device 10 is only one example of a potentially useful bladder. Among the many alternative embodiments, one alternative embodiment of a bladder 140 that may be used in one or more embodiments of tissue compression devices as described herein is depicted in the cross-sectional view of FIG. 9A. The bladder 140 may, in one or more embodiments, be described as a bellows that includes an upper chamber 145 and a lower chamber 146 that are, in the depicted embodiment, aligned along axis 112 extending through the bladder orifice 128 formed in the base 120.

The upper chamber 145 is located adjacent the lower chamber 146 and includes a top layer 191 and a bottom layer 192. The top layer 191 is connected to the bottom layer 192 about an outer perimeter 193 of the upper chamber 145. The outer perimeter 193 may, in one or more embodiments, be formed by a fold in the material used to form the top layer 191 and the bottom layer 192 of the upper chamber 145. The lower chamber 146 includes a top layer 194 and a bottom layer 195. The top layer 194 of the lower chamber 146 is attached to the bottom layer 195 about an outer perimeter 196 of the lower chamber 146. The outer perimeter 196 may, in one or more embodiments, the formed by a fold in the material used to form the top layer 194 and the bottom layer 195 of the lower chamber 146.

The bottom layer 192 of the upper chamber 145 is connected to the top layer 194 of the lower chamber 146. In one or more embodiments, an opening 197 through which the upper chamber 145 is in fluid communication with the lower chamber 146 is provided at the junction between the upper chamber 145 and the lower chamber 146. In one or more embodiments, the bottom layer 192 of the upper chamber 145 and the top layer 194 of the lower chamber 146 may be constructed of a continuous layer of material such that the opening 197 is defined by a fold formed in that material. In one or more alternative embodiments, the bottom layer 192 of the upper chamber 145 and the top layer 194 of the lower chamber 146 may be attached to each other by one or more techniques such as, e.g., welding, adhesives, etc.

Fluid (such as, e.g., gases or liquids) in the upper chamber 145 can pass into or out of the lower chamber 146 through the opening 197 formed between the upper chamber 145 and the lower chamber 146 as described herein. In one or more embodiments, the opening 197 formed between the upper chamber 145 and the lower chamber 146 can be characterized as being smaller than the outer perimeters 193 and 196 of either of the bellows chambers 145 and 146 connected through the opening 197. The size of the opening 197 relative to the outer perimeters of the upper and lower chambers 145 and 146 is described in more detail in connection with FIG. 9B.

The bladder 140 is depicted as being located within the bladder orifice 128 of a tissue compression device as described herein, with the upper chamber 145 located above the bladder orifice 128 and the lower chamber 146 located below the bladder orifice 128. In particular, the upper chamber 145 is located above the top surface 124 of the base 120 such that the bottom layer 192 of the upper chamber faces the top surface 124 of the base 120. The lower chamber 146 is located below the bottom surface 124 of the base 120 such that the top layer 194 of the lower chamber 146 faces the bottom surface 122 of the base 120.

Because the opening 197 is smaller than the outer perimeters 193 and 196 of the upper chamber 145 and lower chamber 146 (respectively) and the bladder orifice 128, the bladder 140 may be retained within the bladder orifice 128 by mechanical interference between the layers of material forming the upper and lower chambers and the upper and lower surfaces of the base 120 regardless of the volume of fluid within the bladder 140. As used herein with respect to bladders retained in the base of a tissue compression device, "mechanical interference" means that one or more of the chambers in a bladder would need to be folded or otherwise deformed from its natural shape (i.e., the shape it takes in the absence of forces acting on it other than ambient air pressure and gravity) to remove the bladder from the bladder orifice in the base.

Figure 9A:
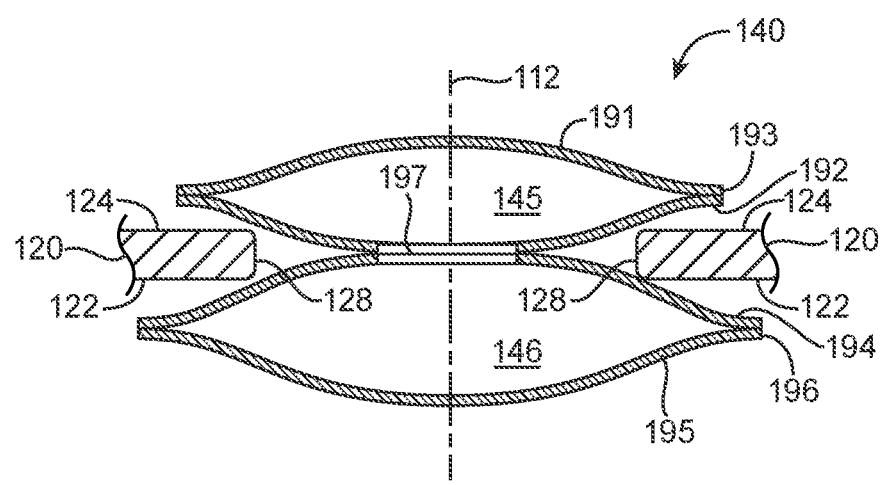
FIG. 9A is a cross-sectional view of an alternative bladder that may be used in one or more embodiments of the tissue compression devices described herein.

In the illustrative embodiment depicted in FIG. 9A, increasing the volume of fluid in the bladder 140 may be described as moving the top layer 191 of the upper chamber 145 away from the top surface 124 of the base 120. Increasing the volume of fluid in the bladder 140 may also be described as moving the bottom layer 195 of the lower chamber 146 away from the bottom surface 122 of the base 120. The top layer 191 can be characterized as forming the upper surface 44 of the bladder 40 depicted in connection with FIGS. 1-8, while the bottom layer 195 can be characterized as forming the lower surface 42 of the bladder 40 depicted in connection with FIGS. 1-8.

Figure 9B:
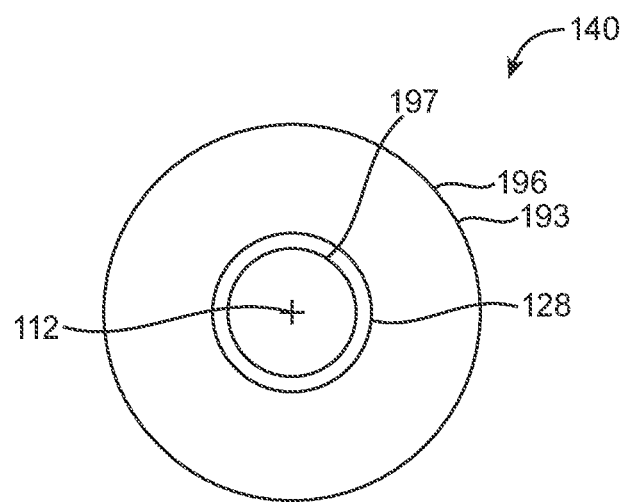
FIG. 9B is a diagram depicting the size and shape of the outer perimeters of the bladder chambers and the bladder orifice depicted in FIG. 9A.

FIG. 9B is a diagram in which the relative sizes and shapes of the outer perimeters of the upper and lower bladder chambers 145 and 146 as well as the bladder orifice 128 provided in the base 120 and the opening 197 between the upper and lower bladder chambers 145 and 146 are depicted. The diagram of FIG. 9B depicts the relative sizes of the outer perimeters 193 and 196, the bladder orifice 128, and the opening 197 as if each of those features is measured in a plane that is transverse to the axis 112. In particular, the diagram depicted in FIG. 9B illustrates that the outer perimeters 193 and 196 of the upper and lower chambers are of the same size and shape (which, in this illustrative embodiment means that the outer perimeters are both generally circular in shape). The bladder orifice 128, which is also depicted in FIG. 9B, has a size that is smaller than both of the outer perimeters 193 and 196. In addition, the size of the opening 197 between the upper and lower bladder chambers 145 and 146 is depicted in FIG. 9B as being smaller than the bladder orifice 128 and either of the outer perimeters 193 and 196 of the upper and lower bladder chambers 145 and 146.

The bladder orifice 128, like the outer perimeters 193 and 196 and the opening 197, also has a generally circular shape, although the bladder orifice 128 may, in one or more alternative embodiments, have a shape that is different than the shape of the outer perimeters of the upper and lower bladder chambers and/or the opening 197 between the upper and lower bladder chambers. For example, the bladder orifice 128 may have a square, rectangular, triangular, etc. shape that is not the same as the shapes of the outer perimeters 193 and 196 of the upper and lower chambers 145 and 146.

Figure 9C:
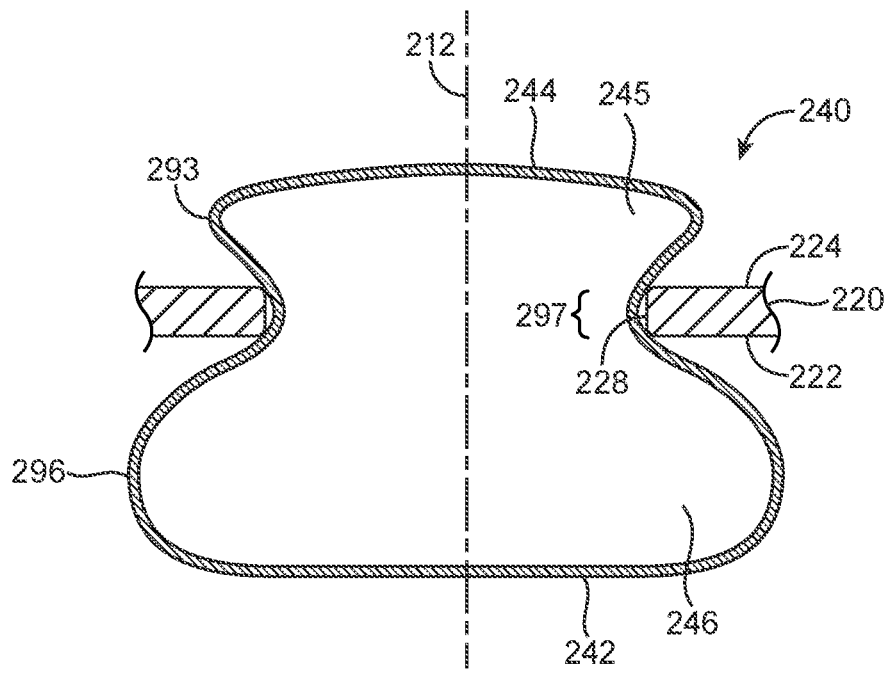
FIG. 9C is a cross-sectional view of another alternative bladder that may be used in one or more embodiments of the tissue compression devices described herein.

Another alternative embodiment of a multi-chamber bladder 240 that may be used in connection with the tissue compression devices described herein is depicted in FIG. 9C. The multi-chamber bladder 240 includes an upper chamber 245 and a lower chamber 246, with a lower surface 242 on the bottom of the lower chamber 246 and an upper surface 244 on the top of the upper chamber 245. As a result, the lower chamber 246 and its lower surface 242 are both located below the bottom surface 222 of the base 220 and the upper surface 244 on the upper chamber 245 are both located above the top surface 224 of the base 220. The upper chamber 245 and the lower chamber 246 are separated from each other by the bladder orifice 228 with the bladder 240 having a necked portion or area 297 located within the bladder orifice 228 formed in the base 220. The upper chamber 245 and the lower chamber 246 are, in the depicted embodiment, aligned along axis 212 which passes through the bladder orifice 228.

In the multi-chamber bladder 140 depicted in FIG. 9A, the upper chamber 145 is formed by sheets of material connected at the outer perimeter 193 of the upper chamber 145 and the lower chamber 146 is formed by sheets of material connected at the outer perimeter 196 of the lower chamber 146. In addition, the layers of material forming the upper and lower chambers 145 and 146 are connected to each other around the opening 197 to form a multi-chamber bladder 140. In contrast, the multi-chamber bladder 240 depicted in FIG. 9C may, in one or more embodiments, be formed in the absence of the variety of separate layers of material joined together to form the chambers in multi-chamber bladders such as multi-chamber bladder 140 depicted in FIG. 9A. For example, in one or more embodiments, a multi-chamber bladder that may be used in the tissue compression devices described herein such as, e.g., multi-chamber bladder 240 may be formed from a single layer of material that may be blow formed or otherwise manufactured to include fewer connections between separate layers.

The multi-chamber bladder 240 depicted in FIG. 9C is, however, like the multi-chamber bladders described elsewhere herein retained within the tissue compression device by mechanical interference between the upper chamber 245 and the lower chamber 246. In particular, both the upper chamber 245 and the lower chamber 246 have outer perimeters that are larger than the bladder orifice 228. As a result, removal of the bladder 240 from the bladder orifice 228 would require a user to manipulate the bladder 240 such that at least one of the outer perimeters of the upper chamber 245 and the lower chamber 246 are small enough to pass through the bladder orifice 228.

Figure 9D:
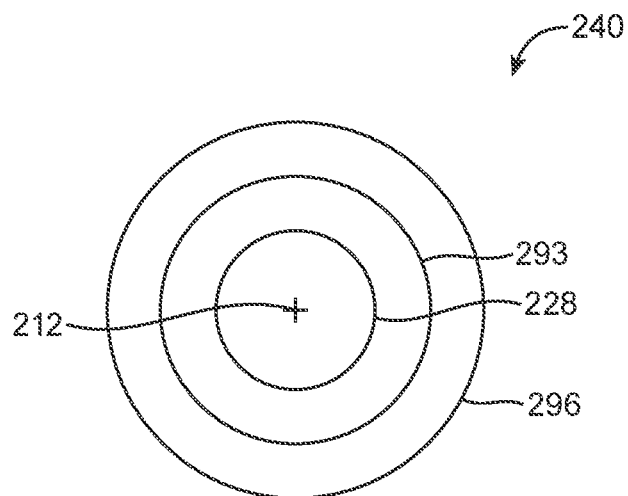
FIG. 9D is a diagram depicting the size and shape of the outer perimeters of the bladder chambers and the bladder orifice depicted in FIG. 9C.

FIG. 9D is a diagram in which the relative sizes and shapes of the outer perimeters of the upper and lower bladder chambers 245 and 246, as well as the bladder orifice 228 provided in the base 220 are depicted (when those features are viewed in the direction of the axis 212). In particular, the diagram depicted in FIG. 9D illustrates that the upper chamber has an outer perimeter 293 that is smaller than the outer perimeter 296 of the lower chamber. The bladder orifice 228, which is also depicted in FIG. 9D, has a size that is smaller than the outer perimeter 293 of the upper chamber and is also smaller than the outer perimeter 296 of the lower chamber. The bladder orifice 228, like the outer perimeters 293 and 296, also has a generally circular shape, although the bladder orifice may, in one or more alternative embodiments, have a shape that is different than the shape of the outer perimeters of the upper and lower bladder chambers as described herein.

Figure 10A:
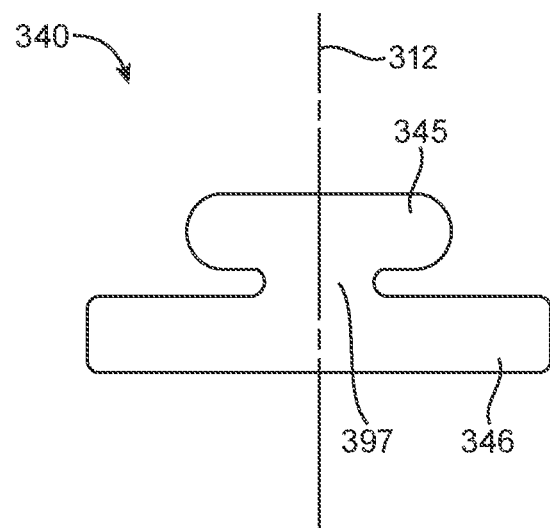
FIG. 10A is a side view of another alternative multi-chamber bladder that may be used in one or more embodiments of the tissue compression devices described herein.
Figure 10B:
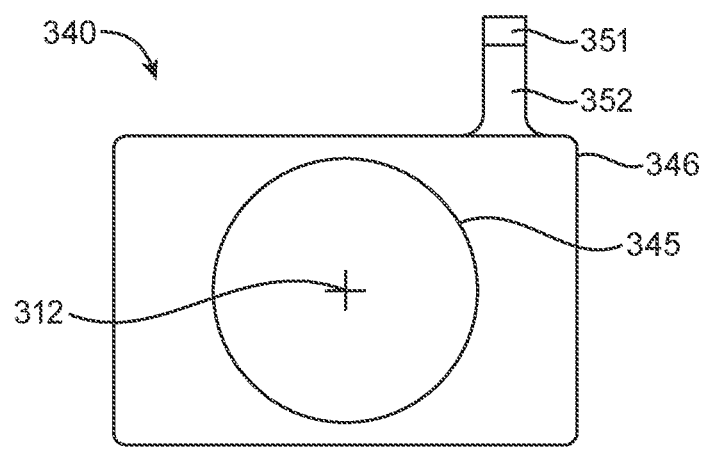
FIG. 10B is a top view of the multi-chamber bladder depicted in FIG. 10A.
Figure 12:
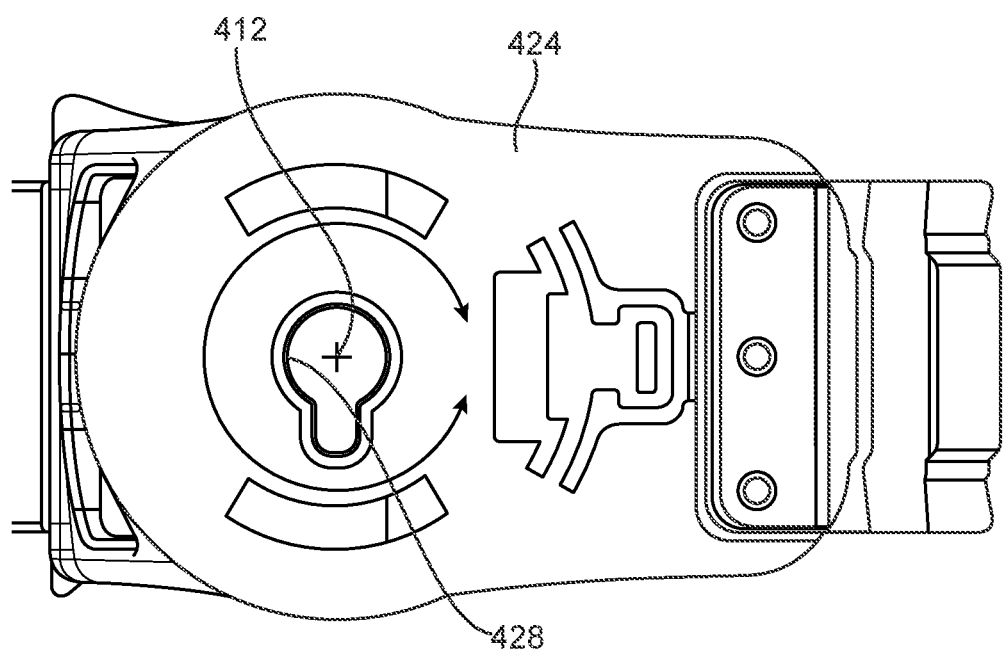
FIG. 12 is a top view of the base 420 of the tissue compression device 410 of FIG. 11, with the bladder removed to allow viewing of the bladder orifice 428.
Figure 13:
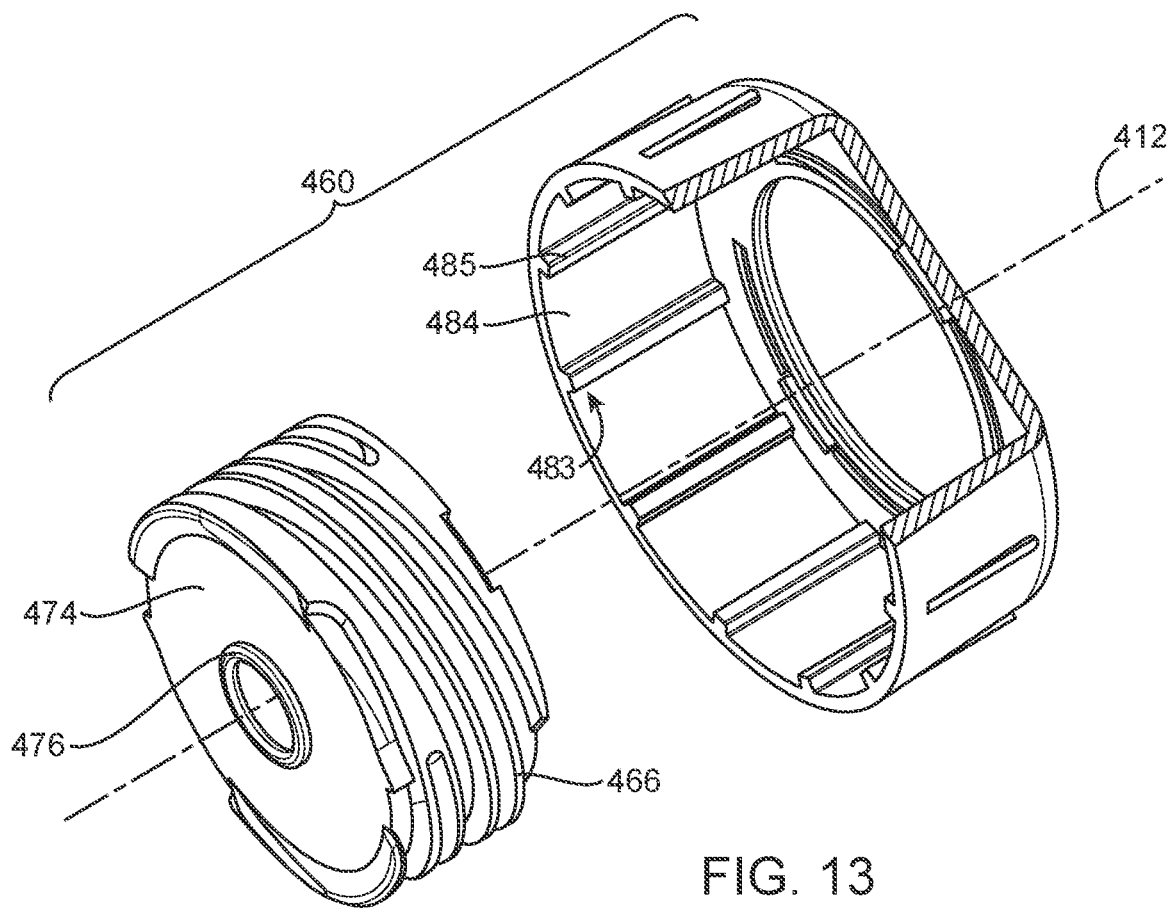
FIG. 13 is an exploded perspective view of the dial 460 of the tissue compression device 410 of FIG. 11.
Figure 14:
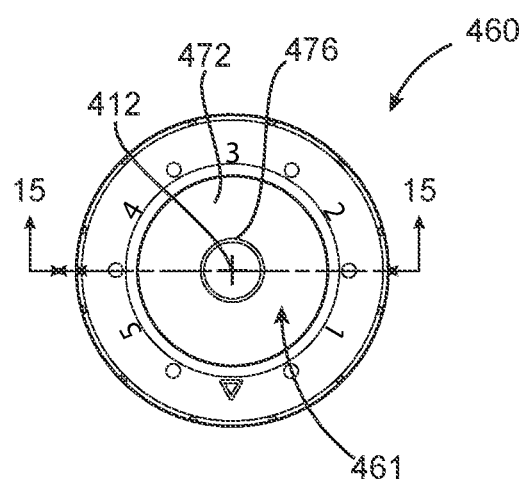
FIG. 14 is a top view of the dial 460 of the tissue compression device 410 of FIG. 11.
Figure 15:
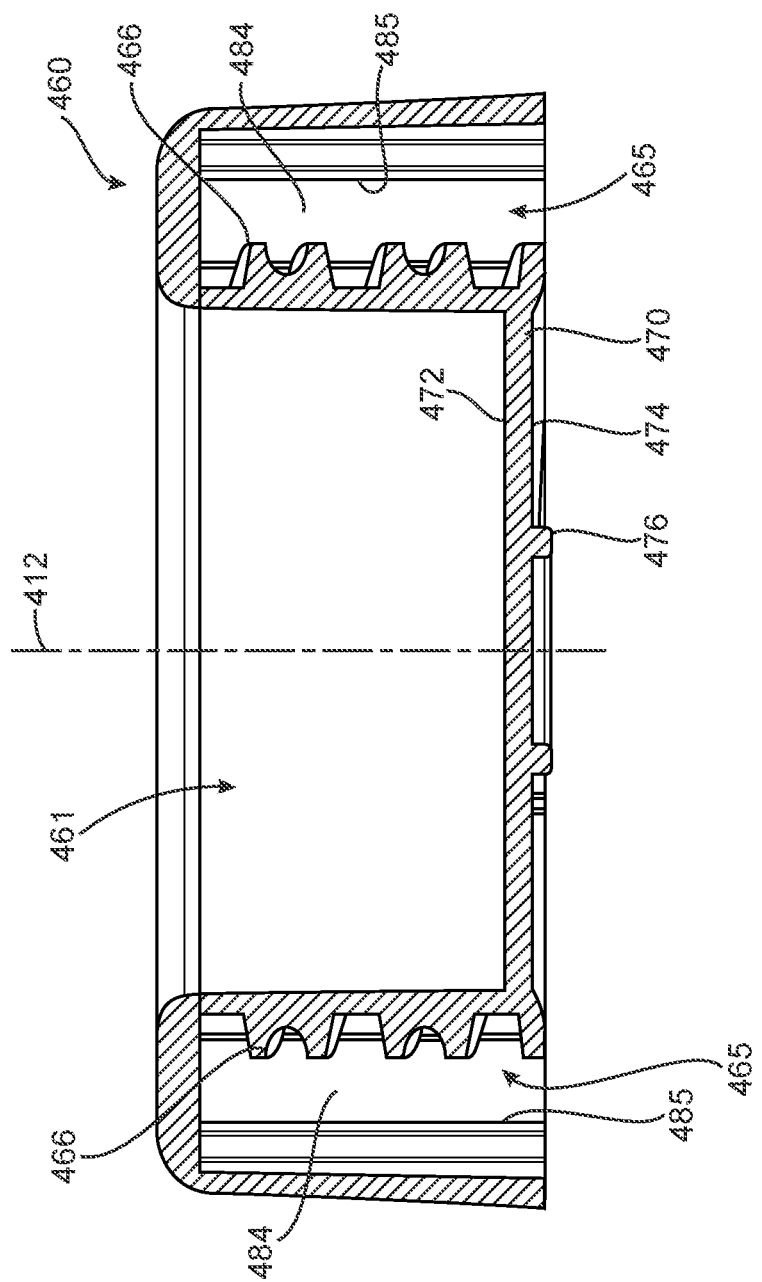
FIG. 15 is a cross-sectional view of the dial 460 taken along line 15-15 in FIG. 14.

Another illustrative embodiment of a multi-chamber bladder is depicted in a side view in FIG. 10A and a top view in FIG. 10B, where the top view is taken along the axis 312 seen in both figures. The multi-chamber bladder 340 includes an upper chamber 345 and a lower chamber 346. The upper chamber 345 is separated from the lower chamber 346 by an opening 397 that is configured to be located in a bladder orifice in the base of a tissue compression device as described herein.

The multi-chamber bladder 340 is provided to illustrate yet another variation that may be provided in the multi-chamber bladders described herein. The multi-chamber bladders described thus far herein may have upper and lower chambers that have outer perimeters with the same shape, e.g., both the upper and lower chambers may have outer perimeters that may be circular or take some other shape (and which may, or may not, be of the same size). In contrast, the multi-chamber bladder 340 depicted in FIGS. 10A and 10B has an upper chamber 345 with an outer perimeter shape that is different than the shape of the outer perimeter of the lower chamber 346.

The different shaped outer perimeters are best seen in the top view of FIG. 10B, where the upper chamber 345 has an outer perimeter that is generally circular in shape, while the lower chamber 346 has an outer perimeter that is rectangular in shape. These shapes as depicted in FIG. 10B are essentially projections of the outer perimeters of the upper and lower chambers 345 and 346 onto a plane that is transverse to the axis 312. The combination of outer perimeter shapes depicted in connection with the illustrative embodiment of multi-chamber bladder 340 is only one example of the many varieties of shapes that could be provided. As a result, the specific shapes depicted in FIGS. 10A and 10B should not be construed to be limiting in any way. For example, the shape of the outer perimeters of the upper and lower bladders may be reversed, i.e., the upper chamber may have a rectangular outer perimeter while the lower chamber may have a generally circular perimeter. Furthermore, the exemplary shapes seen in connection with multi-chamber bladder 340 could be replaced by one or more of any suitable geometric shape (e.g., triangle, square, oval, etc.). In still other embodiments, the outer perimeters of one or more chambers of the bladders used in tissue compression devices described herein may have irregular shapes.

Another optional feature that may be provided in one or more embodiments of the bladders used in the tissue compression devices described herein is the port 351 connected to the bladder 340 by a channel 352. The port 351 may be configured to connect to a fluid delivery device such as, e.g., a syringe, so that fluid can be delivered into or removed from the bladder 340 as described herein. In one or more embodiments, the port 351 may be configured to allow only delivery of fluid into the bladder 340 (e.g., a one-way valve may be provided to prevent escape of fluid from the bladder 340 through the port 351). Although the port 351 is, in the depicted embodiment, connected to the bladder 340 by a channel 352, the port 351 may, in one or more alternative embodiments, be located directly on the bladder 340 such that a channel 352 is not required. Further, although the port 351 and the channel 352 are, in the depicted embodiment, connected to the lower chamber 346 of the bladder 340, in one or more alternative embodiments, the port 351 may be configured to deliver fluid into and/or remove fluid from the upper chamber 345 of the bladder 340.

A perspective view of another illustrative embodiment of a tissue compression device 410 is depicted in FIGS. 11-17. The tissue compression device 410 includes a base 420 and a retention structure 430 attached to the base 420. In the depicted embodiment, the retention structure 430 is in the form of a strap that may be configured to wrap around a limb (e.g., an arm) so that the tissue compression device 410 is placed to compress selected tissue. In the depicted embodiment, the retention structure 430 includes a first end attached to one end of the base 420 and an opposite free end configured to attach to the base 420 as described elsewhere herein. In one or more embodiments, the retention structure 430 may be inextensible as described elsewhere herein. Furthermore, in one or more alternative embodiments, such as the illustrative embodiments depicted in FIGS. 23-27, the tissue compression devices described herein may include a strap retainer on the base 420 that is rigidly or elastically attached to the base and which may, optionally, include a tension indicator as described herein.

The base 420 of the tissue compression device 400 and includes a bottom surface 422 and a top surface 424. The bottom surface 422 of the base 420 is configured to face a limb when retained thereon by the retention structure 430. The top surface 424 of the base 420 faces away from the limb on which the tissue compression device 410 is located.

Also depicted in connection with the exploded perspective view of FIG. 11 is a bladder 440. As with other illustrative embodiments described herein, inflation of the bladder 440 will, in one or more embodiments, tend to move the lower surface of the bladder 440 away from the base 420. When the base 420 is restrained on a limb by, e.g., the retention structure 430, inflation of the bladder will force the lower surface of the bladder 440 against the skin of a patient and, thereby, provide compression of selected tissue (e.g., tissue at an access site, etc.) that is in contact with the lower surface of the bladder 440. That compression, when applied at an access site can, in one or more embodiments, provide hemostasis.

Figure 16:
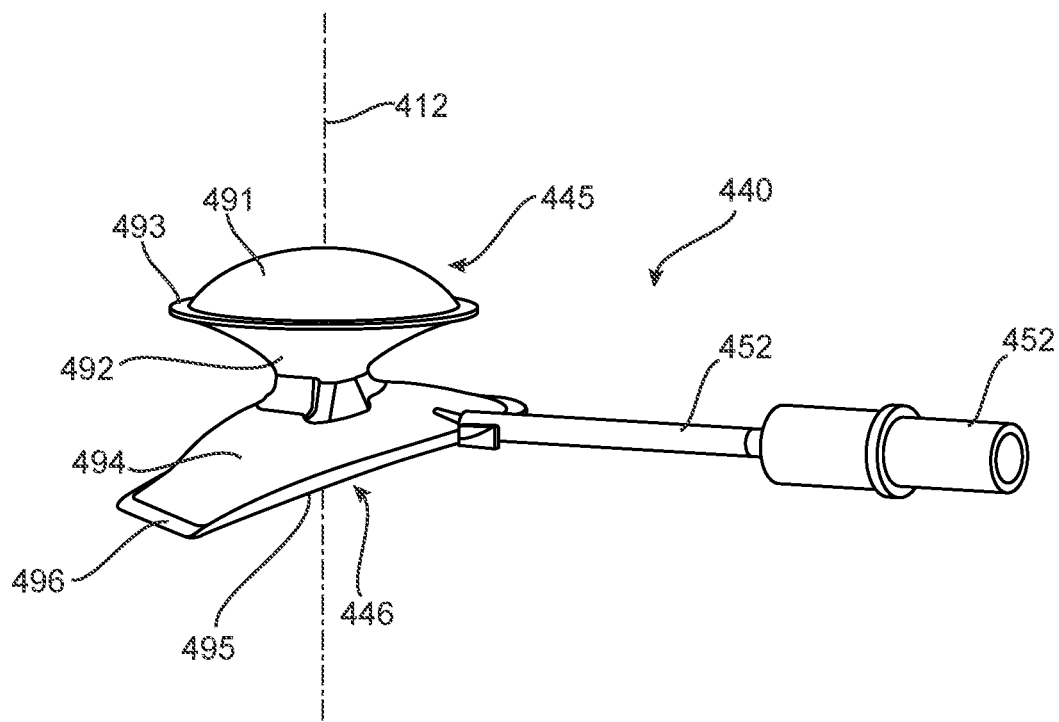
FIG. 16 is a perspective view of the bladder 440 of tissue compression device 410, with the bladder 440 removed from the tissue compression device 410 and inflated.

In the depicted embodiment of tissue compression device 410, the bladder 440 includes an upper chamber 445 and a lower chamber 446 has seen in, e.g., FIGS. 11 and 16. The bladder 440 also includes, in the depicted embodiment, a port 451 connected to the bladder 440 through a channel 452. The port 451 may be configured to connect with a fluid delivery device such as, e.g., a syringe, etc. so that fluid can be delivered into and/or removed from the bladder 440 as described herein. Further, although the port 451 and the channel 452 are, in the depicted embodiment, connected to the lower chamber 446 of the bladder 440, in one or more alternative embodiments the port 451 may be configured to deliver fluid into and/or remove fluid from the upper chamber 445 of the bladder 440.

The bladder 440 in the depicted embodiment of tissue compression device 410 is, in one or more embodiments, attached to the base 420 in a manner similar to that described above in connection with tissue compression device 10. In particular, the upper chamber 445 of the bladder 440 may be located above the top surface 424 of the base 420 while the lower chamber 446 of the bladder 440 may be located below the bottom surface 422 of the base 420 such that the lower chamber 446 is located between the base 420 and the skin of a patient on which the tissue compression device 410 is located. In such an arrangement, the connection between the upper chamber 445 and the lower chamber 446 of the bladder 440 may be located within a bladder orifice 428 formed in the base 420 (see, e.g., FIG. 12). As described herein, the bladder orifice 428 may, in one or more embodiments, be formed through the base 420 from its bottom surface to its top surface 424.

The depicted embodiment of tissue compression device 410 also includes a dial 460 that is attached to the base 420 above the top surface 424. Whether or not the bladders of tissue compression devices described herein are inflated using a separate device or have a fixed volume of fluid located therein, the dial 460 may be used to increase and/or decrease the amount of compression delivered by the tissue compression device 410. In particular, the dial 460 may be rotated about a compression axis 412 to increase or decrease the compression provided by the bladder 440. In one or more embodiments, the compression axis 412 extends through the upper chamber 445 of the bladder 440, the bladder orifice 428 in the base 420 and the lower chamber 446 of the bladder 440 when the base is retained over selected tissue (on, e.g., a limb) by the retention structure 430.

In the depicted embodiment of tissue compression device 410, the dial 460 may be retained on the base 420 by dial posts 462 that extend upward from the top surface 424 of the base 420. In one or more embodiments, the dial posts 462 are arranged around a perimeter of the bladder orifice 428 formed through the base 420. Any number, shape, and/or size of dial posts sufficient to retain the dial 460 on the base 420 and to provide for its rotation as described herein is acceptable.

The depicted embodiment of tissue compression device 410 also includes a stop member 481 that is operably connected to a stop member release lever 480. Movement of the stop member release lever 480 inwardly toward the compression axis 412 moves the connected stop member 481 inwardly toward the compression axis 412. As described herein, inward movement of the stop member 481 allows for rotation of the dial 460 about the compression axis 412.

In the depicted embodiment of tissue compression device 410, the dial 460 includes a dial channel 465 with an opening facing the top surface 424 of the base 420 when the dial 460 is located over the dial posts 462. The dial posts 462 may include raised ribs that, in one or more embodiments, may be arranged in a helical manner on the dial posts such that they cooperate with helical features 466 located within the dial channel 465 of the dial 460. The raised ribs on the dial posts 462 and the helical features 466 located within the dial channel 465 of the dial 460 are configured to cooperate with each other such that rotation of the dial 460 about compression axis 412 in one direction moves the dial 460 closer to the top surface 424 of the base 420, while rotation of the dial 460 in the opposite direction moves the dial 460 away from the top surface 424 of the base 420.

As the dial 460 moves towards the top surface 424 of the base 120, the bottom surface 474 of the bladder window 470 located within a dial orifice 461 of the dial 460 presses against the upper surface of the upper chamber 445 of the bladder 440 to compress the upper chamber 445 of the bladder 440 between the bottom surface 474 of the bladder window 470 in the dial 460.

Another optional feature depicted in connection with the illustrative embodiment of tissue compression device 410 is the window protrusion 476 that extends away from the bottom surface 474 of the window 470. As a result, the window protrusion 476 is located closer to the top surface 424 of the base 420 than a portion of the bottom surface 474 of the bladder window 470 surrounding the window protrusion 476. The bladder window 470 itself may, in one or more embodiments, be clear or translucent to allow viewing of the bladder 440 located between the bladder window 470 and the top surface 424 of the base 420.

The window protrusion 476 may, in one or more embodiments, further include visible indicia such as a colorant, etc. that may identify the location of the bladder orifice 428 in the base 420. In one or more embodiments, the portion of the bladder window 470 located within the boundaries of the window protrusion 476 may be clear while the surrounding portion may be translucent to focus a user's attention on the area directly beneath the compression axis 412 which, in one or more embodiments, also extends through the window protrusion 476. Further, in one or more embodiments the window protrusion 476 may define a perimeter on the surface of a patient's skin over which blood may be allowed to flow when the tissue compression devices described herein are in proper use. For example, the flow of blood past the boundaries of the window protrusion 476 may indicate that pressure should be increased, while the presence of no blood within the boundaries of the window protrusion 476 may indicate that pressure is too high and should be decreased.

Rotation of the dial 460 about the compression axis 412 on the tissue compression device 410 may, in one or more embodiments, be limited or prevented by features as described herein. In the depicted embodiment of tissue compression device 410, the structures that limit or prevent rotation of the dial 460 include the stop member 481 which, as described above, is attached to the stop member release lever 480. The stop member 481 itself is located within the dial channel 465 when the tissue compression device 410 is assembled and is, therefore, inaccessible when the dial 460 is located on the base 420. As a result, a user manipulates the stop member release lever 480 to move the stop member 481 within the dial channel 465.

The stop member 481 prevents or limits rotation of the dial 460 about the compression axis 412 because the stop member 481 is configured to engage with slots 484 that are provided in the outer wall 483 of the dial channel 465. In particular, the slots 484 are bounded on each side by raised portions 485 as seen in, e.g., FIGS. 13 and 15. The stop member 481 fits within one or more of the slots 484 and rotation of the dial 460 about compression axis 412 is limited and/or prevented by the raised portions 485 found on each side of the slots 484 as described herein in connection with this and other illustrative embodiments of the tissue compression devices described herein.

In particular, the stop member release lever 480 is configured such that movement of the stop member release lever 480 towards the compression axis 412 moves its associated stop member 481 out of engagement with the slots 484 in the dial channel 465. In a design such as that depicted in the illustrative embodiment of FIGS. 11-17, a user may be required to place a thumb on the stop member release lever 480 or on the side of the base 420 opposite the stop member release lever 480 and a finger on the feature not occupied by the thumb, such that compression of the thumb and finger towards each other across the dial 460 is required to move the stop member release lever 480 towards the compression axis 412 to release the dial 460 for rotation. This design also potentially provides the advantage of requiring use of two hands, i.e., one hand to move the stop member release lever 480 and its associated stop member out of engagement with slots 484 in the dial channel 465 while a second hand is used to rotate the dial 460 about the compression axis. As a result, a patient wearing the tissue compression device 410 on, e.g., an arm, would not typically be able to rotate the dial 460 to adjust the compression provided by the device 410 themselves because the hand of the limb on which the tissue compression device 410 is located will not be able to reach the dial 460 and/or the stop member release lever 480. As a result the tissue compression device 410 may be a device in which pressure cannot be readily adjusted by a patient wearing the tissue compression device on an arm.

Figure 17:
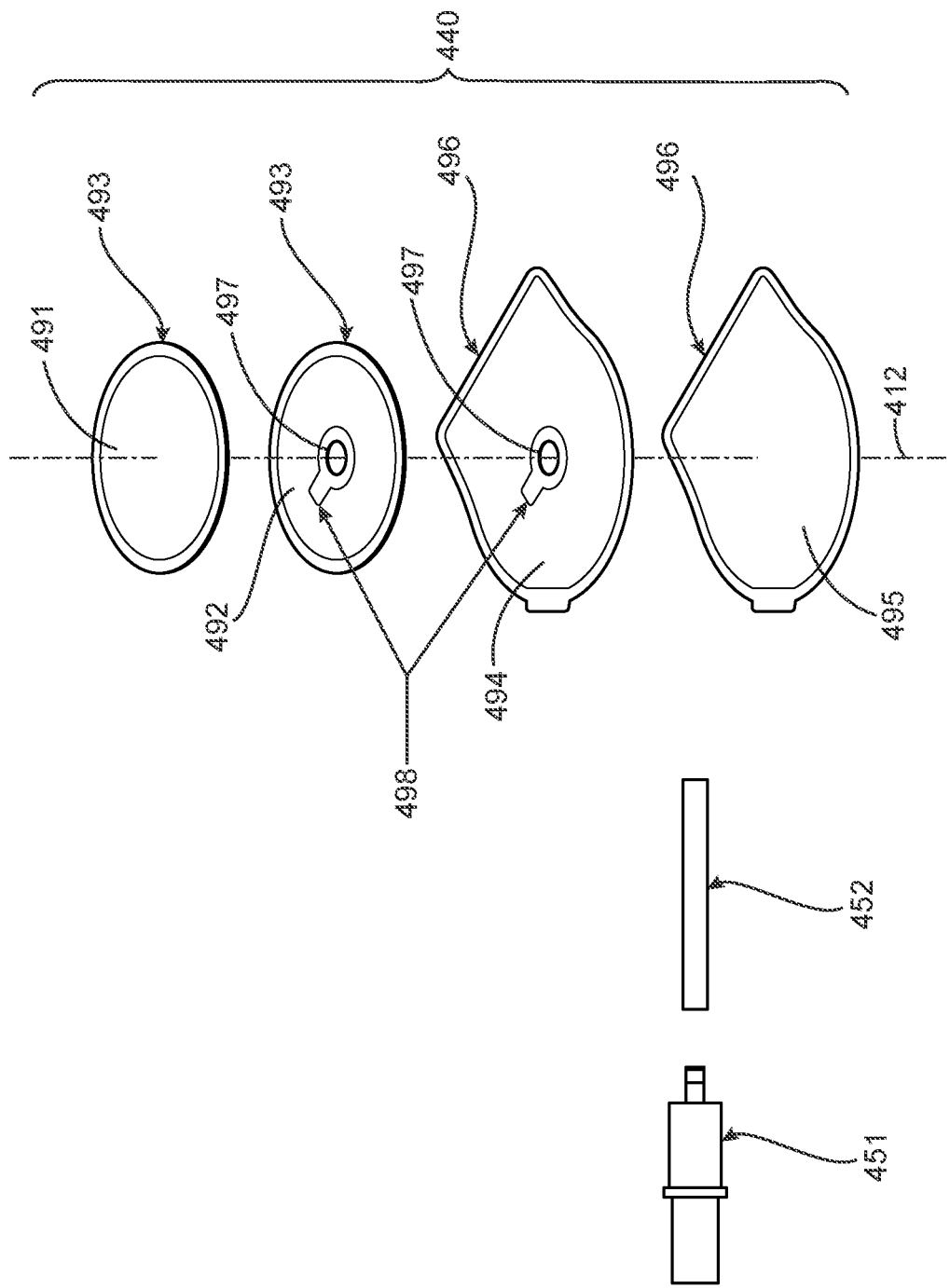
FIG. 17 is an exploded view of components used to construct the illustrative embodiment of bladder 440 as depicted in, e.g., FIG. 16.

The illustrative embodiment of tissue compression device 410 includes a bladder 440 that is seen in FIG. 11 in the exploded view of the device 410, depicted separately in FIG. 16 in an inflated state, and the components used to construct this illustrative embodiment of a bladder that may be used in tissue compression devices as described herein is depicted in an exploded diagram in FIG. 17.

The upper chamber 445 is located adjacent the lower chamber 446 and includes a top layer 491 and a bottom layer 492. The top layer 491 is connected to the bottom layer 492 about an outer perimeter 493 of the upper chamber 445. The top layer 491 may be connected to the bottom layer 492 along the outer perimeter 493 using any suitable technique or combination of techniques (e.g., one or more of adhesives, thermal welding, chemical welding, clamps, etc.). The outer perimeter 493 of the upper chamber 445 is identified in both the top layer 491 and the bottom layer 492 in the exploded diagram of FIG. 17. The lower chamber 446 includes a top layer 494 and a bottom layer 495. The top layer 494 of the lower chamber 446 is attached to the bottom layer 495 about an outer perimeter 496 of the lower chamber 446. The top layer 494 may be connected to the bottom layer 495 along the outer perimeter 496 using any suitable technique or combination of techniques (e.g., one or more of adhesives, thermal welding, chemical welding, clamps, etc.). The outer perimeter 496 of the lower chamber 446 is identified in both the top layer 494 and the bottom layer 495 in the exploded diagram of FIG. 17.

The bottom layer 492 of the upper chamber 445 is connected to the top layer 494 of the lower chamber 446. In one or more embodiments, an opening 497 through which the upper chamber 445 is in fluid communication with the lower chamber 446 is provided at the connection/junction between the upper chamber 445 and the lower chamber 446. The opening 497 is provided in both the bottom layer 492 of the upper chamber 445 and the top layer 494 of the lower chamber 446. In one or more embodiments, the bottom layer 492 of the upper chamber 445 and the top layer 494 of the lower chamber 446 may be attached to each other by one or more techniques such as, e.g., adhesives, thermal welding, chemical welding, clamps, etc.

Fluid (i.e., one or more gases and/or liquids) in the upper chamber 445 can pass into or out of the lower chamber 446 through the opening 497 formed between the upper chamber 445 and the lower chamber 446 as described herein. In one or more embodiments, the opening 497 can be characterized as being smaller than the outer perimeters 493 and 496 of either of the bellows chambers 445 and 446.

The bladder 440 spans the bladder orifice 428 of the tissue compression device 410 as described herein, with the upper chamber 445 located above the bladder orifice 428 and the lower chamber 446 located below the bladder orifice 428. In particular, the upper chamber 445 is located above the top surface 424 of the base 420 such that the bottom layer 492 of the upper chamber 446 faces the top surface 424 of the base 420. The lower chamber 446 is located below the bottom surface of the base 420 such that the top layer 494 of the lower chamber 446 faces the bottom surface of the base 420. In one or more embodiments, the bottom layer 492 of the upper chamber 445 can be described as forming an upwardly directed conical shape when the bladder 440 is inflated, while the top layer 494 of the lower chamber 446 forms a downwardly directed conical shape when the bladder 440 is inflated.

Another optional feature included in the illustrative embodiment of tissue compression device 410 is the addition of a seal line 498 along which the bottom layer 492 of the upper chamber 445 is attached to the top layer 494 of the lower chamber 446. The opening 497 is smaller than the seal line 498 such that the opening 497 is contained within and surrounded by the seal line 498. In one or more embodiments, the seal line 498 may be fluid-tight such that the bottom layer 492 of the upper chamber 445 need not be attached to the top layer 494 of the lower chamber 446 about the periphery of the opening 497.

The bladder and base of the tissue compression devices described herein may include complementary features designed to limit or prevent rotation of the bladder relative to the base about the compression axis. In one or more embodiments, for example, the seal line 498 along which the bottom layer 492 of the upper chamber 445 is connected to the top layer 494 of the lower chamber 446 may be asymmetric about at least one line when the seal line 498 is projected onto a plane transverse to the compression axis 412 passing through upper chamber 445 and lower chamber 446 of the bladder 440 and the bladder orifice 428 in the base 420. In one or more embodiments, the seal line 498 may be described as forming a keyhole shape when projected onto a plane transverse to the compression axis 412, although seal lines forming shapes that have at least one line along which they are asymmetric may be used in place of a keyhole shape, e.g., polygons, ovals, ellipses, irregular shapes, etc.

In one or more embodiments, the bladder orifice 428 in the compression device body 420 of a tissue compression device as described herein may have a complementary shape that is also asymmetric about at least one line when projected onto a plane transverse to the compression axis 412. In one or more embodiments, the bladder orifice 428 may be described as forming a keyhole shape when projected onto that plane. In one or more alternative embodiments the bladder orifice is in tissue compression devices as described herein that have at least one line along which they are asymmetric when projected onto planes as described herein may be used in place of a keyhole shape, e.g., polygons, ovals, ellipses, irregular shapes, etc.

The exemplary keyhole shapes for both seal lines 498 and bladder orifice 428 are both asymmetric about at least one line when projected onto a plane transverse to the compression axis 412. One potential advantage of the asymmetric shapes for both seal lines in bladders and bladder orifices as described herein is that rotation of the bladder about a compression axis when the bladder is assembled in the tissue compression device may be limited or prevented because the asymmetry in the keyhole shapes prevents rotation of the bladder 440 about the compression axis 412 due to mechanical interference between the bladder 440 and the bladder orifice 428 in the base 420. This may be useful where, for example, a dial is rotated to adjust compression provided by the tissue compression devices described herein because that dial rotation may impart rotational forces to the upper chamber of the bladder which could in some instances cause corresponding undesired rotation of the bladder (which could, in turn, cause abrasion or twisting of the skin against which the bladder 440 is compressed).

Another optional feature depicted in connection with the bladder 440 used in the illustrative embodiment of tissue compression device 410 are the shapes of the upper and lower chambers of the bladder 440. In particular, the outer perimeter 493 of the upper chamber 445 of the bladder 440 has, in the depicted embodiment, a circular shape when projected onto a plane transverse to the compression axis 412 (which passes through the upper surface 491, the bladder orifice 428, and the bottom surface 495 of the lower chamber 446). It should be understood that although described as having a circular shape, the upper chamber 445 of the bladder 440 may also have a shape that approximates a circular shape such as, e.g., pentagons, hexagons, octagons, etc. Such generally circular shapes fit well within the boundaries defined underneath the dial 460.

While the upper chamber 445 of the bladder 440 has a generally circular shape, the lower chamber 446 of the bladder may be described as having a noncircular shape when projected onto the same plane as the upper chamber 445. In in the illustrative embodiment depicted in, e.g., FIGS. 11, 15, and 16, the lower chamber 446 has a shape that is generally circular along a portion of its perimeter and which also includes a generally straight edge. Such a shape may, in one or more embodiments, provide for increased surface area coverage of the selected tissue to be compressed by a tissue compression device as described herein and, as a result, may, in one or more embodiments, result in easier placement and better performance of the tissue compression devices as described herein.

Figure 18:
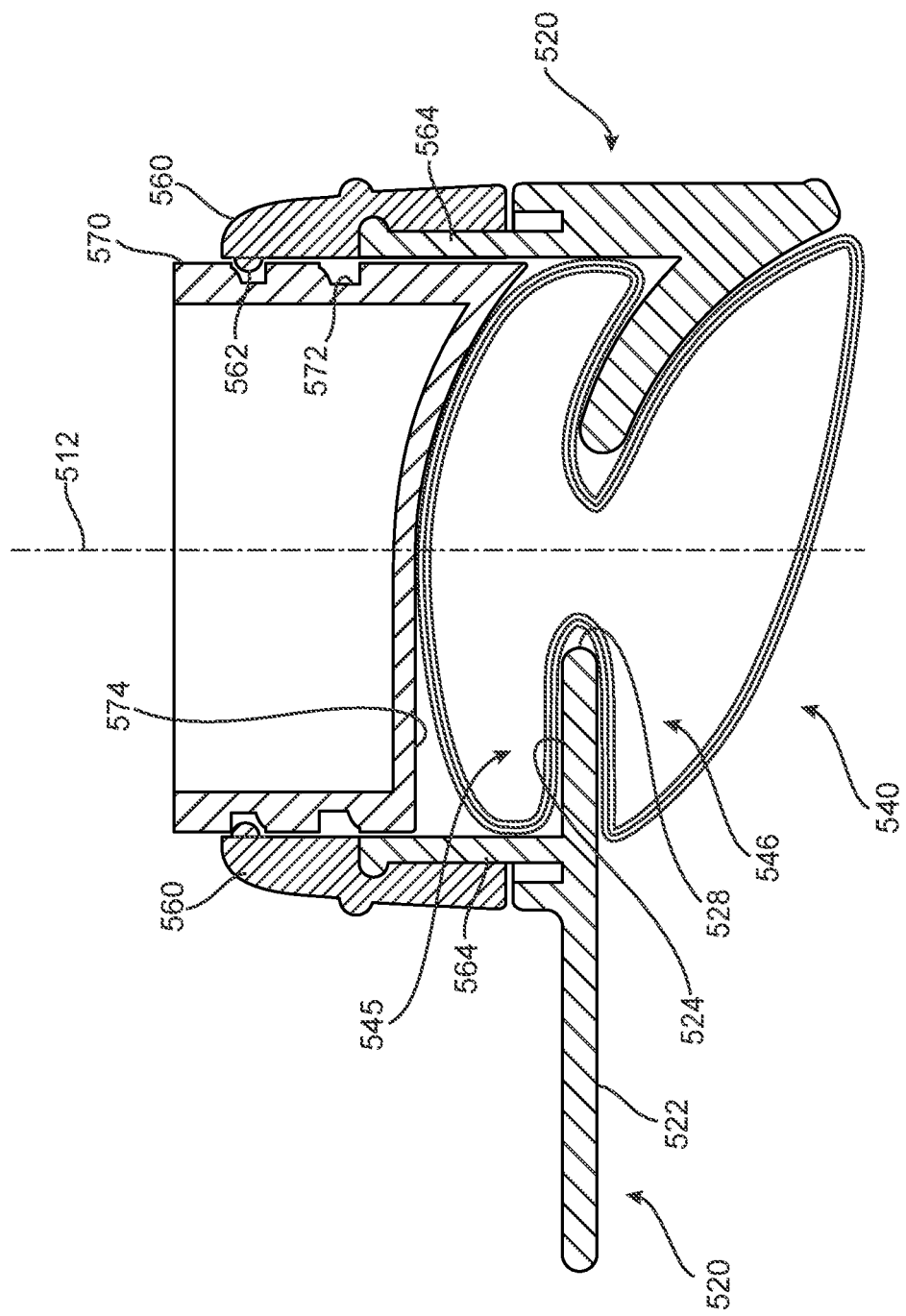
FIG. 18 is a cross-sectional view of another alternative embodiment of a tissue compression device as described herein.

Another illustrative embodiment of a portion of a tissue compression device as described herein is depicted in FIG. 18. In particular, FIG. 18 includes a base 520 having a bottom surface 522 and a top surface 524. A bladder 540 is located within and spans a bladder orifice 528 in the base 520. The bladder 540 includes an upper chamber 545 located above the top surface 524 of the base 520 and a lower chamber 546 located below the bottom surface 522 of the base 520.

Also depicted in FIG. 18 are components designed to compress the upper chamber 545 of the bladder 540. In particular, the base 520 includes dial posts 564 that are configured to receive a rotating dial 560 which rotates about compression axis 512. Rotation of the dial 560 about compression axis 512 does not change the relative height of the dial 560 relative to the base 520. Rather, rotation of the dial 560 about the compression axis 512 moves the window 570 up or down along compression axis 512 as the dial 560 is rotated. In one or more embodiments, such as that illustrated in FIG. 18, the conversion of rotational movement of the dial 562 linear movement of the window 570 is accomplished using complementary threaded structures 562 on the dial 560 and 572 on the window 570.

The window 570 may, in one or more embodiments, include one or more features designed to prevent its rotation relative to the compression axis 512 so that rotation of the dial 560 causes the window 570 to translate up or down along compression axis 512. in one or more embodiments, rotation of the window 570 about compression axis 512 may be limited by the shape of the bottom surface 574 and the shape of top surface 524 of the base 520. In particular, the curved complementary shapes of those two services may, in one or more embodiments, limit or prevent rotation of the window 570 about compression axis 512. Other structures that prevent or limit rotation of the window 570 may be used in place of and/or in addition to the complementary curved surfaces, e.g., slotted structures, etc. may be used to limit rotation of the window 570.

Movement of the window 570 changes the distance between the bottom surface 574 of the window 570 and the upper surface 524 of the base 520, thus changing the allowable volume for the upper chamber 545 of the bladder 540 in between those two surfaces. Reducing that volume can be used as a way to increase pressure within the bladder 540 and, conversely, increasing the volume between the bottom surface 574 of the window 570 and the upper surface 524 of the base 520 may be used as a way to decrease pressure within the bladder 540 as described herein in connection with other embodiments of tissue compression devices.

Figure 19:
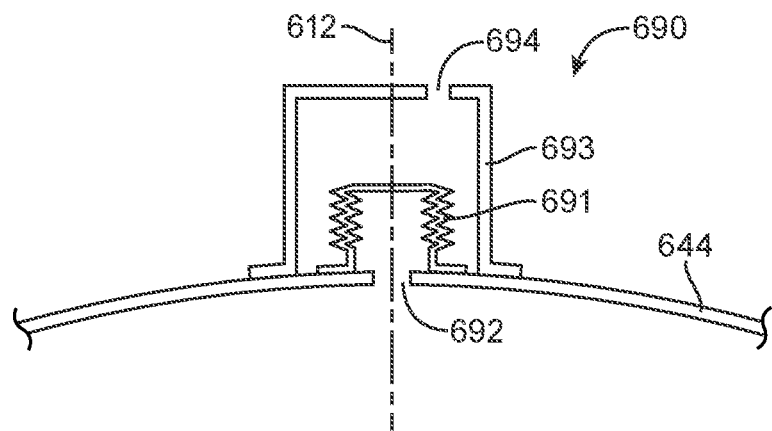
FIG. 19 is a cross-sectional view of one alternative pressure indicator that may be used in the tissue compression devices described herein.
Figure 20:
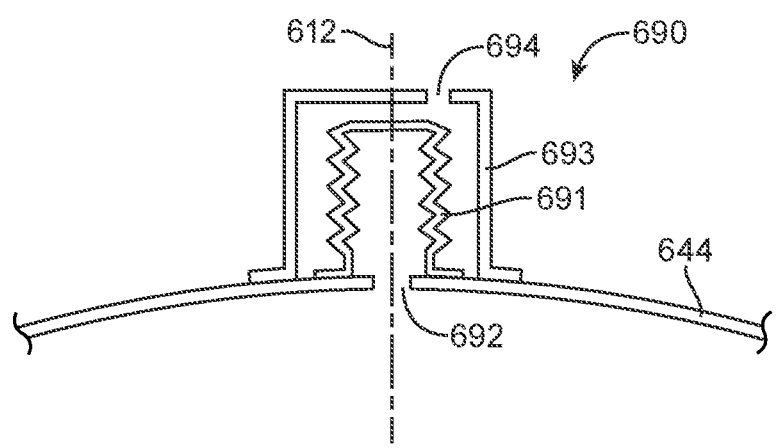
FIG. 20 is a cross-sectional view of the pressure indicator of FIG. 19 with the pressure in the bladder increased as compared to FIG. 19.
Figure 21:
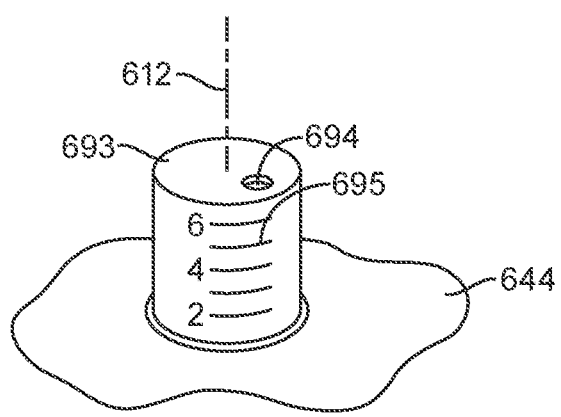
FIG. 21 is a perspective view of the pressure indicator of FIG. 19.

In one or more embodiments of tissue compression devices as described herein, it may be useful to provide some indication as to the pressure being delivered by the tissue compression devices. As discussed herein, the bi-stable ring indicators are only one illustrative embodiment of a pressure indicator that may be used in the tissue compression devices described herein. One alternative embodiment of a pressure indicator that may be used in connection with the tissue compression devices described herein is depicted in FIGS. 19-21.

The pressure indicator 690 is in the form of a bellowed chamber 691 located on the upper surface 644 of a bladder that may be used in a tissue compression device as described herein. The interior of the bellowed chamber 691 is in fluid communication with the interior of the bladder through an opening 692 in the upper surface 644 of the bladder. The bellowed chamber 691 is, in the depicted embodiment, located within a housing 693. The housing 693 may also be attached to the upper surface 644 of the bladder and may further include a vent 694. The vent 694 is used to allow for the escape of air from the housing 693 as the bellowed chamber 691 expands when pressure within the bladder increases. That expansion is depicted in the changes between FIGS. 19 and 20, wherein the bellowed chamber 691 occupies a larger volume of the housing 693 in FIG. 20.

In one or more embodiments, the housing 693 may be transparent or translucent and include indicia 695 to provide a visual reference with respect to the amount of pressure within the bladder. As the bellowed chamber 691 increases in volume, its upper surface will be located at a height that corresponds to a different level of the indicia 695. Because the housing 693 is transparent or translucent, the location of the upper surface of the bellowed chamber 691 can be seen through the housing 693.

Figure 19A:
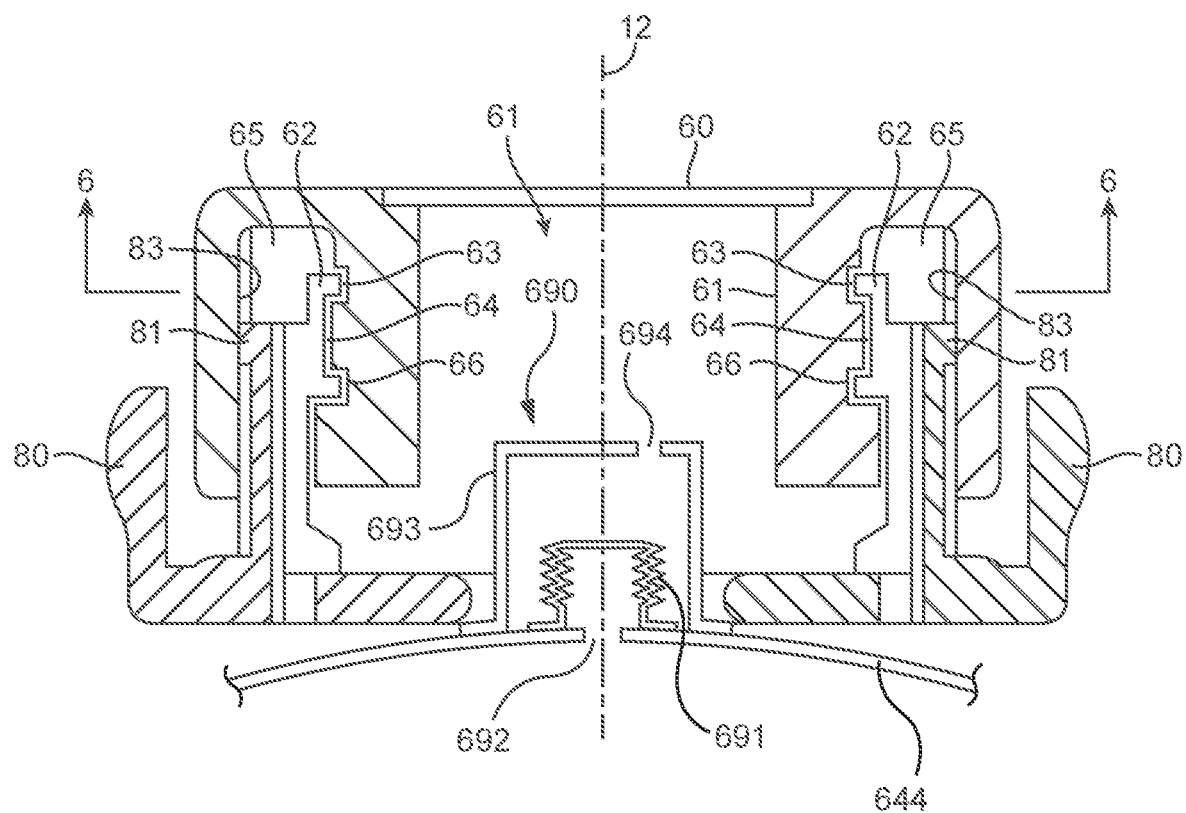
FIG. 19A is a cross-sectional view of the pressure indicator of FIG. 19 located within a dial orifice.

The pressure indicator 690 may, in one or more embodiments, be located within a dial orifice on the upper surface 644 of a bladder located within a tissue compression device as described herein, as shown in FIG. 19A. In one or more embodiments, the pressure indicator 690 may be aligned along the compression axis 612 formed within a tissue compression device as described herein.

Figure 22:
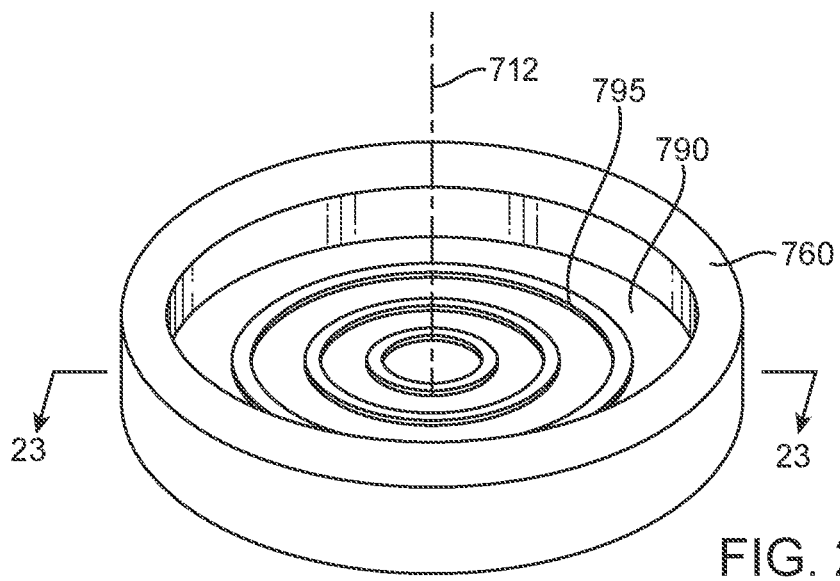
FIG. 22 is a perspective view of another alternative pressure indicator that may be used in the tissue pressure devices described herein.
Figure 23:
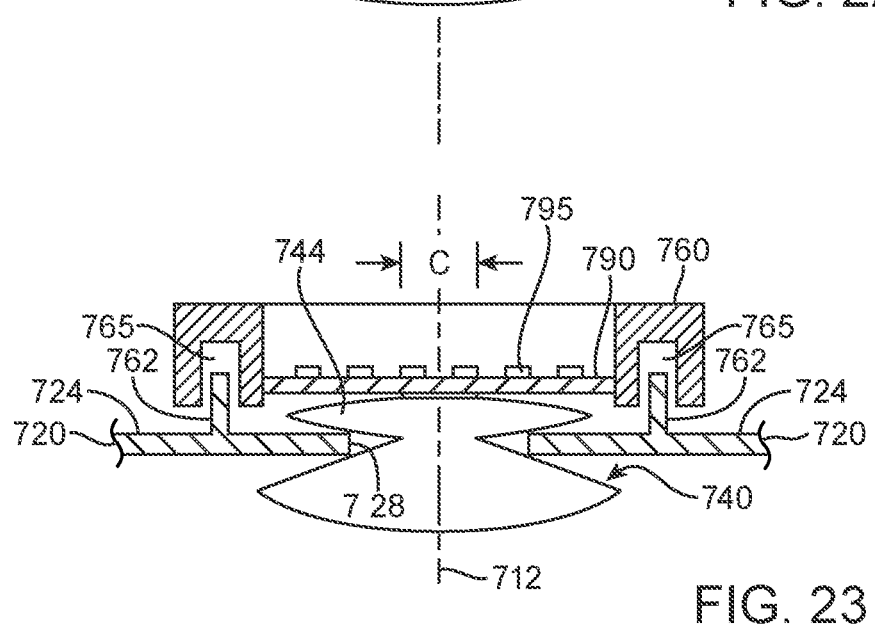
FIG. 23 is a cross-sectional view of the pressure indicator of FIG. 22 taken along line 23-23 in FIG. 22.
Figure 24:
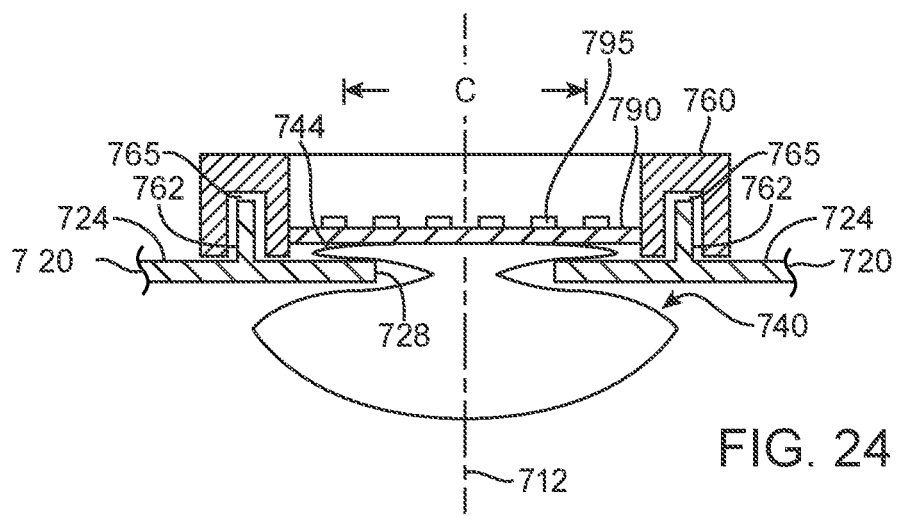
FIG. 24 is a cross-sectional view of the pressure indicator of FIG. 22 with the pressure in the bladder increase as compared to FIG. 23.

Another alternative embodiment of a pressure indicator that may be used in connection with the tissue compression devices described herein is depicted in FIGS. 22-24. In particular, a dial 760 is depicted in FIG. 22 and includes a bladder window 790, with the bladder window being located above the bladder orifice 728 formed in a base 720 as well as above the upper surface 744 of a bladder 740. The bladder window includes indicia 795 which, in one or more embodiments, may be in the form of concentric circles provided on the bladder window 790. In one or more embodiments, such as that depicted in, e.g., FIG. 22, the dial 760 is configured for rotation about a compression axis 712 which is similar to the compression axes described elsewhere herein.

The dial 760 is, in the depicted embodiment, configured for rotation about the compression axis 712 using dial posts 762 extending upwardly from the upper surface 724 of a base 720 and into the dial channel 765 as depicted in FIGS. 23-24. As with the dials described in the illustrative embodiments described above, the dial 760 may be rotated towards or away from the upper surface 724 of the base 720 to increase or decrease pressure within the bladder 740.

The illustrative embodiment of the pressure indicator depicted in FIGS. 22-24 provides an indication of the pressure being applied by the bladder 740 of the tissue compression device based on the amount of the upper surface 744 of the bladder 740 that is in contact with the underside of the bladder window 790. The contact area between the upper surface 744 of the bladder 740 and the bladder window 790 may be indicated in FIGS. 23-24 by the dimension C provided in each of those figures. In particular, the smaller contact area indicated by the smaller dimension C in FIG. 23 may be indicative of a lower pressure within the bladder 740 as compared to the larger contact area indicated by the larger dimension C in FIG. 24.

The indicia 795 provided on or in the bladder window 790 may be useful in providing a visual indicator of the amount of contact between the upper surface 744 of the bladder 740 and the bladder window 790. A larger portion of the upper surface 744 of the bladder 740 contacts the bladder window 790 when pressure in the bladder 740 is increased. Conversely, a smaller portion of the upper surface 744 of the bladder 740 contacts the bladder window 790 when the pressure in the bladder 740 is decreased. The indicia 795 may, in one or more embodiments, provide a convenient way of visually determining the amount of increase or decrease in the portion of the upper surface 744 of the bladder 740 that is in contact with the bladder window 790 as pressure in the bladder is changing. That visual determination can be made by noting the increase or decrease in the number/amount of indicia 795 located within the area of the bladder window 790 that is contacted by the upper surface 744 of the bladder 740.

Although the indicia 795 is depicted as being located on the bladder window 790 in the illustrative embodiment of FIGS. 22-24, in one or more alternative embodiments, indicia may be provided on the upper surface 744 of the bladder 740 in addition to, or in place of the indicia on the bladder window 790. Indicia provided on the upper surface 744 of the bladder 740 may, in one or more embodiments, provide a convenient way of visually determining the amount of increase or decrease in the portion of the upper surface 744 of the bladder 740 that is in contact with the bladder window 790 as pressure in the bladder is changing. That visual determination can be made by noting the increase or decrease in the number/amount of indicia on the upper surface 744 of the bladder 740 that are in contact with the bladder window 790.

In one or more alternative embodiments, the upper surface of the bladder window 790 may be provided with a matte finish, anti-reflective coating, etc. that is configured to reduce specular reflection from the upper surface of the bladder window 790 (where the upper surface of the bladder window 790 is the surface facing away from the bladder 740). In one or more embodiments, any matte finish, anti-reflective coating, etc. provided on the upper surface the bladder window 790 may reduce specular reflection from the upper surface of the bladder window of visible light by 50% or more (when the upper surface of the bladder window 790 is provided in a planar or flat configuration). In one or more alternative embodiments, the bladder window 790 may be provided with some curvature (either concave or convex) to reduce specular reflection experienced by a viewer viewing the upper surface of the bladder window 790. Regardless of the feature or features used to reduce specular reflection, any such features should not unduly hinder visibility of the tissue located beneath the bladder 740.

Additional features that may be included in one or more embodiments of the tissue compression devices described herein are depicted in connection with FIGS. 25-28. Those additional features may include a strap retainer that is elastically attached to the base of the tissue compression device, as well as a tension indicator that may, in one or more embodiments, limit the travel distance between the strap retainer and the base of the tissue compression devices as described herein.

The illustrative embodiment of tissue compression device 810 includes a pressure apparatus 840 on a base 820 that is configured to be attached to a patient using a strap 830 having a first end 832 attached to one end 821 of the base 820. A strap retainer 801 is attached to the opposite end of the base 820 and includes a slot 826 or other opening configured to receive and retain the strap 830. Because the strap 830 is attached to opposite ends of the base 820, the strap 830 can be used to encircle a limb or other portion of a patient's anatomy to retain the tissue compression device 810 on the patient.

The strap 830 may, in one or more embodiments, include fasteners (e.g., hook and loop fasteners, interlocking mechanical fasteners, buckles, snaps, etc.) that are configured to allow the strap 830 to form a loop for attachment to the strap retainer 801. Alternatively, the strap 830 and strapped retainer 801 may include features configured to form a connection or attachment between the strap 830 and the strap retainer 801. For example, the strap retainer 801 may be in the form of a buckle, the strap 830 and strap retainer 801 may include snaps or other complementary features that enable attachment of the strap 832 the strap retainer 801. In still other embodiments, the strap 830 and strap retainer 801 may include other complementary connection apparatus such as, e.g., hook and loop fasteners, interlocking mechanical fasteners, etc.

In the depicted embodiment, the strap retainer 801 has a slot 826 that includes an optional opening 827 into the slot 826. The opening 827 allows the strap 830 to slide into the slot 826 during placement of the tissue compression device 810. As a result, the opening 827 may simplify attachment of the strap 830 to the strap retainer 801 because the free end 834 of the strap 830 need not be threaded through a hole in the strap retainer 801 in order to secure it.

When the strap 830 is attached to the strap retainer 801, the base 820 and the strap 830 cooperate to retain the pressure apparatus 840 of the tissue compression device 810 over a selected location on a patient, e.g., an access site, etc. Although the depicted embodiment of tissue compression device 810 includes a pressure apparatus 840 that may be similar in construction to the pressure apparatus described in other illustrative embodiments of tissue compression devices described herein, other forms of pressure apparatus may also be used in conjunction with tissue compression devices including elastically attached strap retainers as described herein.

In one or more embodiments, the strap 830 may be inextensible along its length such that when the strap 830 is attached to the strap retainer 801, the distance along the length of the strap 830 between the first end 821 of the base 820 and the strap retainer 801 does not change as tension along the strap 830 increases during normal use of the tissue compression device 810.

As described herein, however, the strap retainer 801 is attached to one end of the base 820 by an elastic member 802. As a result, the strap retainer 801 moves away from the base 820 in response to tension forces applied to the strap retainer 801 by the strap 830. In one or more embodiments, the strap retainer 801 and elastic member 802 may be described as being configured to draw the strap retainer 801 towards the base 820 against any tension forces applied to the strap retainer 801 by, e.g., the strap 830.

The elastic member 802 may take a variety of different forms, e.g., elastic member 802 may be a woven and/or nonwoven elastic construction similar to straps used on, e.g., clothing, luggage, etc. In one or more alternative embodiments, the elastic member 802 may be in the form of a solid elastic construction, e.g., the elastic member 802 may be in the form of a solid body of, e.g., an elastomeric polymer, rubber, latex, etc. In still other alternative embodiments, the elastic member 802 may be in the form of a composite structure. Regardless of the specific construction of the elastic member 802, it may, in one or more embodiments, be configured to provide a biasing force that draws the strap retainer 801 towards the base 820 of the tissue compression devices described herein.

In addition to the elastic member, a tension indicator may also be provided in one or more embodiments of the tissue compression devices described herein. The tension indicator 803 depicted in the illustrative embodiments seen in FIGS. 25-28 may, in one or more embodiments, provide feedback to a user regarding the tension force exerted between the base 820 and the strap retainer 801 by the elastic member 802. In the depicted embodiment, the tension indicator 803 includes a fixed end 806 attached to the strap retainer 801 and a traveling end 804 located distal from the fixed end 806 of the tension indicator 803. The tension indicator 803 passes through a slot 805 in the base 820 and is configured to move through the slot 805 as the strap retainer 801 moves towards and away from the base 820. Although the depicted embodiment of tension indicator 803 moves through a slot 805 in the base 820, in one or more alternative embodiments, the tension indicator 803 may not be required to move through a slot. For example, the tension indicator may merely move relative to the base of the tissue compression device without being required to pass through a slot.

While the elastic member 802 is elastically extensible in response to tension forces applied to the elastic member 802 as described herein, the tension indicator 803 may, in one or more embodiments, be in the form of an inextensible member (i.e., does not stretch or change in length during normal use of the tissue compression devices described herein).

In one or more embodiments, the tension indicator 803 may be in the form of a separate and discrete article from the elastic member 802. This separate and discrete construction may be seen in, e.g., the cross-sectional view depicted in FIG. 26, where the elastic member 802 and the tension indicator 803 are located next to each other but are not attached to each other except for their connection through the strap retainer 801 and/or the base 820.

The tension indicator 803 may, in one or more embodiments, provide feedback to a user regarding the tension force exerted between the base 820 and the strap retainer 801 by the elastic member 802 in one or more of a variety of ways. For example, in one or more embodiments, feedback regarding the tension force exerted between the base 820 and the strap retainer 801 by the elastic member 802 may be indicated by the relative positions between the strap retainer 801, the base 820 and the tension indicator 803. In one or more embodiments, visible indicia that may be provided on the base 820 and/or the tension indicator 803 to assist the user in monitoring the tension force exerted between the base 820 and the strap retainer 801 by the elastic member 802. In one or more embodiments, both visible indicia and the relative positions described herein may be used to provide feedback to user regarding the tension force.

The relative positions between the strap retainer 801, the base 820 and the tension indicator 803 may, in one or more embodiments, be correlated to a tension force applied by the elastic member 802 between the strap retainer 801 and the base 820. In particular, the correlation between tension force and distance between the strap retainer 801 and base 820 may be a function of the spring constant of the elastic member 802, i.e., the tension force supplied by the elastic member 802 increases as the elastic member 802 is elongated and, conversely, the tension force supplied by the elastic member 802 decreases as the elastic member 802 is allowed to retract or shorten its length.

In one or more embodiments, the tension indicators provided in conjunction with the tissue compression devices described herein may be configured to limit the travel distance over which the strap retainers move relative to the bases of the tissue compression devices in response to tension forces exerted on the strap retainers by the straps. In the illustrative embodiment depicted in connection with, e.g., FIG. 25, the travel distance over which the strap retainer 801 can move relative to the base 820 may, in one or more embodiments, be limited by the tension indicator 803 to a selected travel distance.

In the depicted embodiment, the tension indicator 803 limits travel distance to a selected travel distance through the use of a structural stop 804 on the tension indicator 803. The structural stop 804 is configured to limit movement between the base 820 and the strap retainer 801 to the selected travel distance through mechanical interference between the slot 805 in which the tension indicator 803 moves and the structural stop 804 on the tension indicator. In particular, the structural stop 804 is of a size and/or shape that restricts movement of the structural stop 804 through the slot 805. As a result, after the strap retainer 801 is moved away from the base 820 by the distance between the structural stop 804 and the strap retainer 801, further movement of the strap retainer 801 away from the base 820 is prevented because the structural stop 804 cannot pass through the slot 805.

Figure 25:
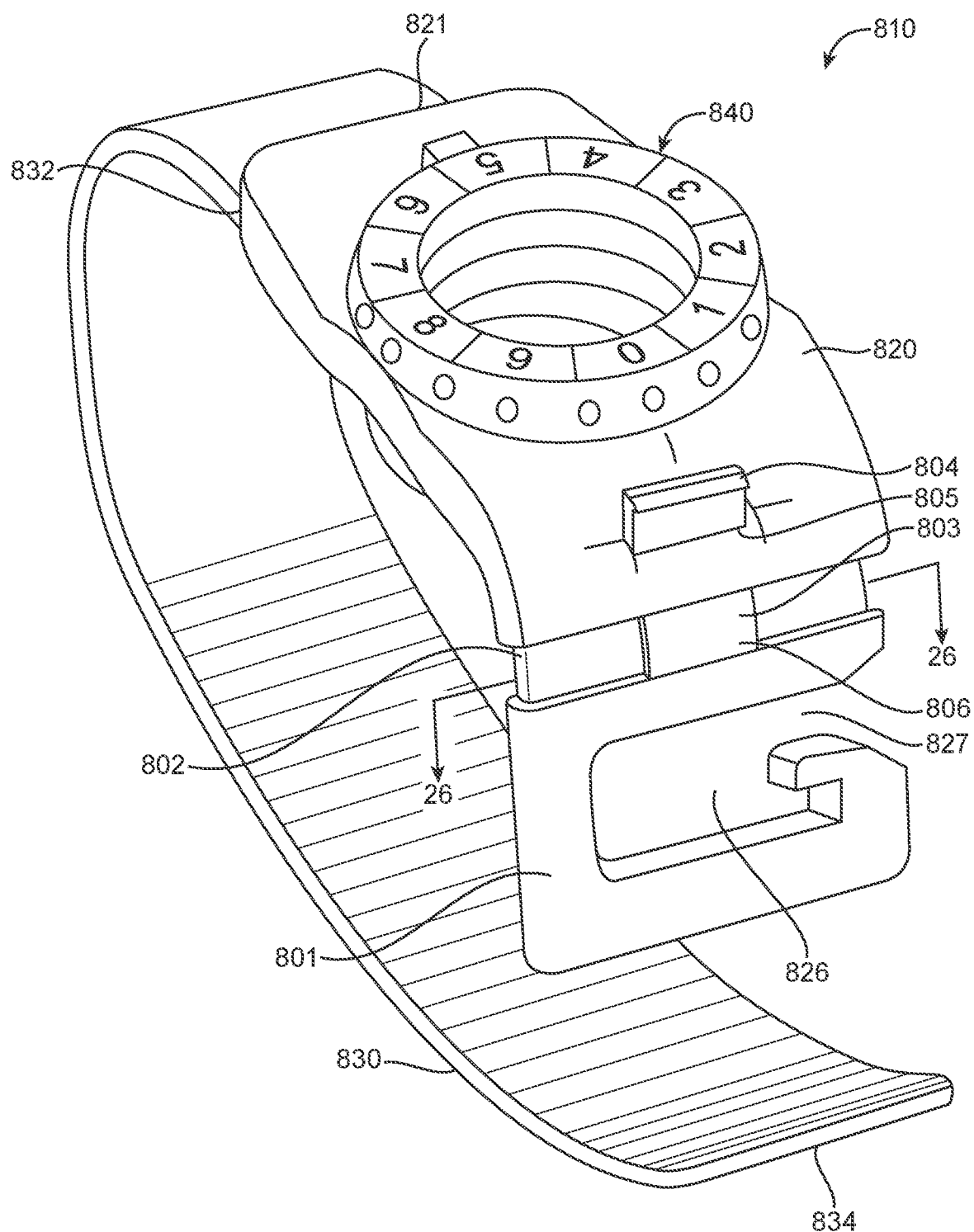
FIG. 25 is a perspective view of one illustrative embodiment of a tissue compression device including a strap retainer attached to the base of the device by an elastic member, the device further including a tension indicator.
Figure 26:
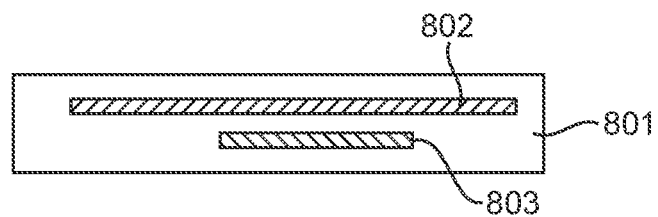
FIG. 26 is a cross-sectional view of the tissue compression device of FIG. 25 taken along line 26-26 in FIG. 25.

The size and/or shape of the structural stop 804 and the slot 805 as seen in the illustrative embodiment depicted in FIG. 25 are only one example of structures that can provide mechanical interference to limit travel distance between a base and a strap retainer of a tissue compression device as described herein.

Further, in one or more alternative embodiments, the distance between the structural stop 804 and the fixed end 806 of the tension indicator 803 (i.e., the end attached to the strap retainer 801) may be adjusted to change the selected tension force provided by the elastic member 802 when the structural stop 804 reaches the slot 805 (or has its travel otherwise limited). Such an adjustment may be made by providing the structural stop 804 in the form of a collar, plug, etc. that can be moved to different locations along the tension indicator 803.

Furthermore, although the tension indicator 803 is described as having a fixed end 806 attached to the strap retainer 801 and extending through a slot 805 in the base 820 of a tissue compression device 810, alternative embodiments may involve a reverse configuration in which the fixed end of the tension indicator is attached to the base and extends through a slot or similar feature located within the strap retainer. In either case, the tension indicator can, in one or more embodiments, provide both an indication of tension force exerted by the elastic member extending between the strap retainer and the base, as well as, optionally, limiting travel distance as described herein.

In one or more embodiments of tissue compression devices as described herein, the use of a tension indicator that limits travel distance to a selected travel distance may be advantageous. In particular, the limited travel distance may provide feedback to user that a selected tension force is being applied by the tissue compression device around a limb or other anatomical feature of a patient. With that baseline force being set by the interactions between the strap and elastically attached strap retainer, adjustment of the pressure apparatus 840 associated with the tissue compression device 810 can and/or should be used to adjust the compressive force being delivered to a selected location as described herein.

Figure 27:
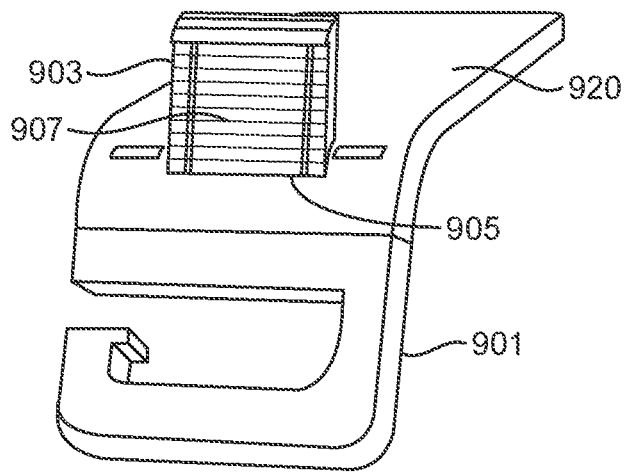
FIG. 27 is an isolated view of another illustrative embodiment of a portion of a base of a tissue compression device including a strap retainer attached to the base by elastic member and a tension indicator, with the strap retainer being held in a retracted configuration.
Figure 28:
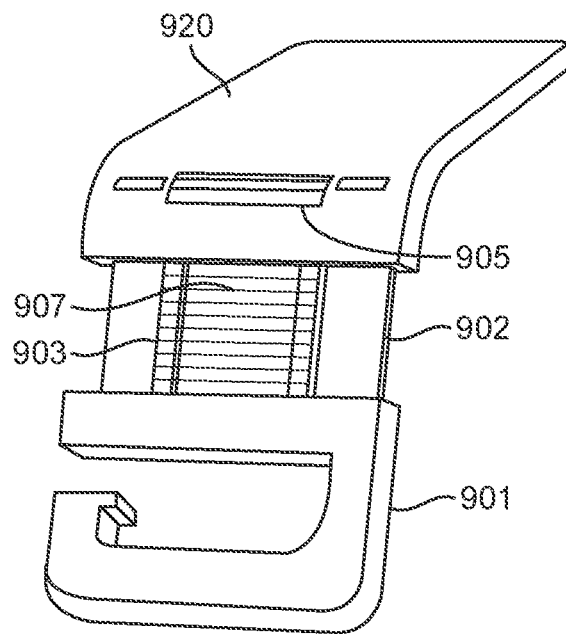
FIG. 28 is a view of a portion of the base of a tissue compression device as seen in FIG. 27, with the strap retainer being held in an extended configuration.

Another illustrative embodiment of a strap retainer 901 attached to a base 920 of a tissue compression device is depicted in FIGS. 27-28 in both a retracted position and an extended position. In particular, the strap retainer 901 is in its retracted position with respect to base 920 in FIG. 27, while the strap retainer 901 is in its extended position in FIG. 28. A comparison of these two figures shows that the strap retainer 901 is located farther away from the base 920 when in the extended configuration of FIG. 28 than when in the retracted configuration of FIG. 27.

The strap retainer 901 is attached to the base 920 by an elastic member 902. A tension indicator 903 extends through a slot 905 in the base 920, and the tension indicator 903 slides or moves through the slot 905 as the strap retainer 901 moves between its retracted and extended positions.

In one or more embodiments, the tension indicator 903 may be provided with one or more visible indicia 907 that indicate the position of the tension indicator 903 and, therefore, the position of the attached strap retainer 901, relative to the base 920 of a tissue compression device as described herein. The visible indicia 907 on the tension indicator 903 may be provided in a variety of different forms including, but not limited to, shaded or colored areas, gradation marks, etc.

Disclosure of any patents, patent documents, and publications identified herein are incorporated by reference in their entirety as if each were individually incorporated. To the extent there is a conflict or discrepancy between this document and the disclosure in any such incorporated document, this document will control.

Illustrative embodiments of the tissue compression devices or methods are discussed herein some possible variations have been described. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof. It should also be understood that this invention also may be suitably practiced in the absence of any element not specifically disclosed as necessary herein.

What is claimed is:

1. A tissue compression device comprising:
    a base and a retention structure attached to the base, the retention structure configured to retain the base over selected tissue at a selected location;
    a bladder operably attached to the base, wherein a lower surface of the bladder faces the selected tissue when the retention structure retains the base over the selected location, and wherein an upper surface of the bladder faces away from the lower surface of the bladder; and
    a pressure indicator, wherein the pressure indicator comprises:
        a bellowed chamber comprising a top surface that is configured to move closer to the upper surface of the bladder when pressure in the bladder is reduced and farther away from the upper surface of the bladder when pressure in the bladder is increased, and
        an indicator housing positioned on the upper surface of the bladder, wherein the bellowed chamber is located in the indicator housing and visible through the indicator housing, wherein a position of the top surface of the bellowed chamber in the indicator housing is indicative of pressure in the bladder.

2. A device according to claim 1, wherein the indicator housing comprises visible indicia arrayed along a side surface, wherein the visible indicia is indicative of pressure in the bladder.

3. A device according to claim 1, wherein the indicator housing is attached to the upper surface of the bladder.

4. A device according to claim 1, wherein an interior of the bellowed chamber is in fluid communication with an interior of the bladder through an opening in the upper surface of the bladder.

5. A device according to claim 1, wherein the bladder includes a port connected to the bladder through a channel and configured to allow for fluid delivery into the bladder and for fluid removal from the bladder.

6. A device according to claim 1, wherein the indicator housing includes a vent allowing for the escape of air from the indicator housing as the bellowed chamber expands when pressure within the bladder increases.

7. A device according to claim 1, wherein the bladder includes an upper chamber positioned adjacent to a lower chamber.

8. A device according to claim 7, wherein the bladder includes an opening through which the upper chamber is in fluid communication with the lower chamber.

9. A tissue compression device comprising:
   a base and a retention structure attached to the base, the retention structure configured to retain the base over selected tissue at a selected location;
   a bladder operably attached to the base, wherein a lower surface of the bladder faces the selected tissue when the retention structure retains the base over the selected location, and wherein an upper surface of the bladder faces away from the lower surface of the bladder; and
   a pressure indicator, wherein the pressure indicator comprises:
      a bellowed chamber in communication with an interior of the bladder, the bellow chamber comprising a top surface that is configured to move closer to the upper surface of the bladder when pressure in the bladder is reduced and farther away from the upper surface of the bladder when pressure in the bladder is increased, and
      an indicator housing, wherein the bellowed chamber is located in the indicator housing and visible through the indicator housing, wherein a position of the top surface of the bellowed chamber in the indicator housing is indicative of pressure in the bladder,
   wherein the base comprises a bottom surface and a top surface, wherein the base comprises a bladder orifice formed through the base from the bottom surface to the top surface, wherein the bellowed chamber and the indicator housing of the pressure indicator are located within a perimeter of the bladder orifice.

10. A device according to claim 9, wherein the device defines a compression axis extending through the upper surface of the bladder, the bladder orifice in the base, and the lower surface of the bladder when the base is retained over the selected location by the retention structure, and wherein the top surface of the bellowed chamber moves along the compression axis when pressure in the bladder is reduced or increased.

11. A device according to claim 9, wherein the bladder includes an upper chamber positioned adjacent to a lower chamber.

12. A device according to claim 11, wherein the bladder includes an opening through which the upper chamber is in fluid communication with the lower chamber.

13. A device according to claim 11, wherein the upper chamber of the bladder is located above a top surface of the base while the lower chamber of the bladder is located below a bottom surface of the base such that the lower chamber is located between the base and the selected tissue.

14. A device according to claim 11, wherein a connection between the upper chamber of the bladder and the lower chamber of the bladder is located within the bladder orifice formed in the base.

15. A tissue compression device comprising:
   a base and a retention structure attached to the base, the retention structure configured to retain the base over selected tissue at a selected location;
   a dial coupled to a top surface of the base the dial including a dial orifice;
   a bladder operably attached to the base, wherein a lower surface of the bladder faces the selected tissue when the retention structure retains the base over the selected location, and wherein an upper surface of the bladder faces away from the lower surface of the bladder; and
   a pressure indicator located in the dial orifice, wherein the pressure indicator comprises:
      a bellowed chamber in communication with an interior of the bladder, the bellow chamber comprising a top surface that is configured to move closer to the upper surface of the bladder when pressure in the bladder is reduced and farther away from the upper surface of the bladder when pressure in the bladder is increased, and
      an indicator housing, wherein the bellowed chamber is located in the indicator housing and visible through the indicator housing, wherein a position of the top surface of the bellowed chamber in the indicator housing is indicative of pressure in the bladder,
   wherein the base further comprises a bottom surface and a bladder orifice formed through the base from the bottom surface to the top surface, wherein the bellowed chamber and the indicator housing of the pressure indicator extend through the bladder orifice and into the dial orifice.

16. A device according to claim 15, wherein the bladder includes an upper chamber positioned adjacent to a lower chamber.

17. A device according to claim 16, wherein the bladder includes an opening through which the upper chamber is in fluid communication with the lower chamber.

18. A device according to claim 16, wherein the upper chamber of the bladder is located above the top surface of the base while the lower chamber of the bladder is located below the bottom surface of the base such that the lower chamber is located between the base and the selected tissue.

* * * * *